(12) United States Patent
Hu et al.

(10) Patent No.: US 7,535,224 B2
(45) Date of Patent: May 19, 2009

(54) DISCRETE MAGIC ANGLE TURNING SYSTEM, APPARATUS, AND PROCESS FOR IN SITU MAGNETIC RESONANCE SPECTROSCOPY AND IMAGING

(76) Inventors: Jian Zhi Hu, 365 Hanford St., Richland, WA (US) 99354; Jesse A. Sears, Jr., 604 Canyon Lakes Dr., Kennewick, WA (US) 99337; David W. Hoyt, 1921 McMurray Ave., Richland, WA (US) 99354; Robert A. Wind, 7918 W. 21st Ave., Kennewick, WA (US) 99338

( * ) Notice: Subject to any disclaimer, the term of this patent is extended or adjusted under 35 U.S.C. 154(b) by 79 days.

(21) Appl. No.: 11/754,660

(22) Filed: May 29, 2007

(65) Prior Publication Data
US 2008/0297157 A1   Dec. 4, 2008

(51) Int. Cl.
*G01V 3/00* (2006.01)
(52) U.S. Cl. ...................... 324/307; 324/321
(58) Field of Classification Search ............... 324/307, 324/309, 321
See application file for complete search history.

(56) References Cited

U.S. PATENT DOCUMENTS

| | | | | |
|---|---|---|---|---|
| 5,170,120 A | * | 12/1992 | Barbara et al. | 324/307 |
| 5,208,536 A | * | 5/1993 | Cory | 324/321 |
| 6,184,683 B1 | * | 2/2001 | Emsley et al. | 324/309 |
| 6,653,832 B2 | * | 11/2003 | Wind et al. | 324/307 |
| 6,670,811 B2 | * | 12/2003 | Wind et al. | 324/307 |
| 6,989,674 B2 | * | 1/2006 | Wind et al. | 324/321 |

OTHER PUBLICATIONS

Andrew ER, Eades RG, Removal of dipolar broadening of NMR spectra of solids by specimen rotation. Nature 183, 1802 (1959).

Cheng LL, Ma MJ, Becerra L, Ptak T, Tracey I, Lackner A, and Gonzalez RG. Quantitative neuropathology by high resolution magic angle spinning proton magnetic resonance spectroscopy. Proc. Natl. Acad. Sci. USA. 94, 6408-6413 (1997).

Bollard ME, Garrod S, Holmes E, Lindon JC, Humpfer E, Spraul M, and Nicholson JK. High-resolution 1H and 1H-13C Magic Angle Spinning NMR Spectroscopy of Rat Liver, Magn. Reson. Med 44, 2901-207 (2000).

Chen J, Enloe BM, Fletcher CD, Cory DG, Singer S. Biochemical analysis using high-resolution magic angle spinning NMR spectroscopy distinquishes lipoma-like well-differentiated liposarcoma from normal fat. J. Am. Chem. Soc. 123, 9200-9201 (2001).

(Continued)

*Primary Examiner*—Louis M Arana

(57) ABSTRACT

Described are a "Discrete Magic Angle Turning" (DMAT) system, devices, and processes that combine advantages of both magic angle turning (MAT) and magic angle hopping (MAH) suitable, e.g., for in situ magnetic resonance spectroscopy and/or imaging. In an exemplary system, device, and process, samples are rotated in a clockwise direction followed by an anticlockwise direction of exactly the same amount. Rotation proceeds through an angle that is typically greater than about 240 degrees but less than or equal to about 360 degrees at constant speed for a time applicable to the evolution dimension. Back and forth rotation can be synchronized and repeated with a special radio frequency (RF) pulse sequence to produce an isotropic-anisotropic shift 2D correlation spectrum. The design permits tubes to be inserted into the sample container without introducing plumbing interferences, further allowing control over such conditions as temperature, pressure, flow conditions, and feed compositions, thus permitting true in-situ investigations to be carried out.

49 Claims, 11 Drawing Sheets

OTHER PUBLICATIONS

Garrod S, Humpher E. Spraul M, Connor SC, Polley S, Connelly J, Lindon JC, Nicholson JK, Homes E. High-resolution magic angle spinning 1H NMR spectroscopic studies on intact rat renal cortex and medulla. Magn. Reson. Med. 41, 1108-1118 (1999).

Garrod S, Humpher E, Connor SG, Connelly JC, Spraul M, Nicholson JK and Holmes E. High-resolution 1H NMR and magic angle spinning NMR spectroscopic investigation of the biochemical effects of 2-bromoethanamine in intact renal and heptic tissue. Magn. Reson. Med. 45, 781-790 (2001).

Weybright P, Millis K, Campbell N, Cory DG, and Singer S. Gradient, high-resolution, magic angle spinning 1H nuclear magnetic resonance spectroscopy of intact cells. Magn. Reson. Med. 39, 337-345 (1998).

Taylor JL, Wu CL, Cory D, Gonzalez RG, Bielecki A, Cheng LL, High-resolution magic angle spinning proton NMR analysis of human prostate tissue with slow spinning rates, Magn. Reson. Med. 50, 627-632 (2003).

Bollard ME, Stanley EG, Lindon JC, Nicholson JK and Holmes E. NMR-based metabonomic approaches for evaluating physiological influences on biofluid composition. NMR in Biomedicine 18; 143-162 (2005).

Nicholson JK, Wilson ID. High resolution 1H NMR spectroscopy of biological fluids. Prog. NMR Spectrosc. 21, 449-501 (1989).

Griffin JL. Metabolic profiles to define the genome: can we hear the phenotypes? Phil. Trans. R. Soc. Lond. B 359, 857-871 (2004).

Lindon JC, Nicholson JK, Holmes E, Everett JR. Metabonomics: Metabolic processes studies by NMR spectroscopy of biofluids. Concepts Magn. Reson. 12, 289-320 (2000).

A. Bax, N. M. Szeverenyi, and G. E. Maciel, Correlation of isotropic shifts and chemical shift anisotropies by two-dimensional Fourier-transform magic angle hopping NMR spectroscopy. J. Magn. Reson. 52 (1983) 147-152.

N. M. Szeverenyi, A. Bax and G. E. Maceil, Magic-angle Hopping as an alternative to magic angle spinning for solid state NMR, J. Magn. Reson. 61, 440-447 (1985).

C. Keeler, J. Xiong, H. Lock, S. Dec, T. Tao, and G. E. Maciel, A new in situ chemical reactor for studying heterogeneous catalysis by NMR: the GRASSHopper, Catalysis Today 49 (1999) 377-383.

J. Z. Hu, A. M. Orendt, D. W. Alderman, C. Ye and R. J. Pugmire, Improvements to the magic angle hopping experiment, Solid State NMR 2 (1993) 235-243.

G. E. Maciel, N. M. Szeverenyi, M. Sardashti. Chemical-shift-anisotropy powder patterns by the two-dimensional angle-flipping approach. Effects of crystallite packing. J. Magn. Reson. 64, 365-374 (1985).

A. Bax, N. Szeverenyi, G. E. Maciel. Chemical shift anisotropy in powdered solids studied by 2D FT NMR with flipping of the spinning axis. J. Magn. Reson. 55, 494-497 (1983).

T. Terao, T. Fujii, T. Onodera, A. Saika. Switching-angle sample-spinning NMR-spectroscopy for obtaining powder-pattern-resolved 2D spectra-measurements of C-13 chemical shift anisotropies in powdered 3,4-dimethoxybenzaldehyde. Chem. Phys. Letts. 107, 145-148 (1984).

T. Nakai, C. A. McDowell. A fast two-dimensional switching-angle sample-spinning method for separating chemical-shift powder patterns. J. Magn. Reson. 93, 618-623 (1991).

A. C. Kolbert, H. J. M. De Groot, R. G. Griffin. Two-dimensional switched-speed spinning NMR. J. Magn. Reson. 85, 60-68 (1989).

R. C. Zeigler, R. A. Wind, G. E. Maciel. The stop-and-go spinning techniques in MAS experiments. J. Magn. Reson. 79, 299-306 (1988).

Z. Gan, High-resolution chemical shift and chemical shift anisotropy correlation in solids using slow magic angle spinning, J. Am. Chem. Soc. 114, 8307-8309 (1992).

Z. Gang, R. R. Ernst, An improved 2D magic-angle-turning pulse sequence for the measurement of chemical-shift anisotropy, J. Magn. Reson A 123, 140-143 (1996).

Z. Gan, Spinning side-band suppression using a pseudo-2-dimensional experiment. J. Magn. Reson. A 109, 253-255 (1994).

G. McGeorge, D.W. Alderman, D.M. Grant, Resolution enhancement in C-13 and N-15 magic-angle turning experiments with TPPM decoupling, J. Magn. Reson. 137, 138-143 (1999).

J. Z. Hu, W. Wang, F. Liu, M. S. Solum, D. W. Alderman, R. J. Pugmire, and D. M. Grant, Magic-angle-turning experiments for measuring chemical-shift-tensor principal values in powdered solids. J. Magn. Reson A 113 (1995) 210-222.

J. Z. Hu, D. W. Alderman, C. Ye, R. J. Pugmire and D. M. Grant. An isotropic chemical shift-chemical shift anisotropy magic-angle slow-spinning 2D NMR experiment. J. Magn. Reson. A 105, 82-87 (1993).

J. Z. Hu, A. M. Orendt, D. W. Alderman, R. J. Pugmire, C. Ye and D. M. Grant. Measurement of 13C chemical shift tensor principal values with a magic-angle turning experiment. Solid State NMR. 3, 181-197 (1994).

D. W. Alderman, G. McGeorge, J. Z. Hu, R. J. Pugmire and D. M. Grant. A sensitive, high resolution magic angle turning experiment for measuring chemical shift tensor principal values. Molecular Physics 95, 1113-1126 (1998).

Antzutkin ON, Shekar SC, and Levitt MH. Two-dimensional sideband separation in magic-angle-spinning NMR. J. Magn. Reson. A115, 7-19 (1995).

A. C. Kolbert, R. G. Griffin, Two-dimensional resolution of isotropic and anisotropic chemical shifts in magic angle spinning NMR. Chem. Phys. Letters 166, 87-91 (1990).

L. Frydman, G.C. Chingas, Y. K. Lee, P. J. Grandinetti, M. A. Eastman, G. A. Barral and A. Pines. Variable-angle correlation spectroscopy in solid-state nuclear magnetic resonance. J. Chem. Phys. 97, 4800-4808 (1992).

A. M. Orendt, J. Z. Hu, Y. J. Jiang, J. C. Facelli, W. Wang, R. J. Pugmire, C. Ye and D. M. Grant. Solid-state C-13 NMR measurements in methoxynaphthalenes: Determination of the substituent chemical shift effects in the principal values. J. Chem. Phys. A 101, 9169-9175 (1997).

J. C. Facilli, J. Z. Hu, A. M. Orendt, A. M. Arif, R. J. Pugmire and D. M. Grant. Solid-state C-13 NMR, x-ray, and quantum-mechanical studies of the carbon chemical-shift tensors of p-tolyl ether. J. Phy. Chem. 98, 12186-12190 (1994).

J. Z. Hu, M. S. Solum, C. M. V. Taylor, R. J. Pugmire and D. M. Grant. Structural determination in carbonaceous solids using advanced solid state NMR techniques. Energy & Fuels 15, 14-22 (2001).

Hu JZ, Rommerein DN, Wind RA. High resolution 1H NMR spectroscopy in rat liver using magic angle turning at a 1 Hz spinning rate. Magn. Reson. Med. 47, 829-836 (2002).

Wind RA, Hu JZ, Rommereim DN. High-resolution 1H NMR spectroscopy in a live mouse subjected to 1.5 Hz magic angle spinning. Magn. Reson. Med. 50, 1113-1119 (2003).

Hu JZ and Wind RA. Sensitivity-enhanced phase corrected ultra-slow magic angle turning using multiple-echo data acquisition. J. Magn. Reson. 163, 149-162 (2003).

Wind RA, Hu JZ, Pajors PD. Slow-MAS NMR: A new technology for in vivo metabolomic studies. Drug Discovery Today: Technologies 2, 291-294 (2005).

Wind RA, Hu JZ, Majors PD. Localized in vivo isotropic-anisotropic correlation 1H NMR spectroscopy using ultraslow magic angle spinning. Magn. Reson. Med. 55, 41-49 (2006).

M. Hunger, T. Horvath, A new MAS NMR probe for in-situ investigation of hydrocarbon conversion on solid catalysts under continuous-flow conditions, J. Chem. Soc. Comm. 1423-1424 (1995).

P. Goguen, J. F. Haw, An in situ NMR probe with reagent flow and magic angle spinning, J. Catal. 161, 870-872 (1996).

\* cited by examiner

Pulse Phases for the SP-DMAT Pulse Sequences

Transmit Frequency, $F^{\pm}$

| Pulse[a] | index | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|---|---|---|---|---|---|---|---|---|---|---|---|---|---|---|---|---|
| a | | -y | +y | -y | -y | +y | -y | -y | +y | -y | -y | +y | -y | -y | +y | -y | +y | -y | +y | -y | +y | -y | +y | -y | +y | -y | +y | -y | +y | -y | +y | -y | +y |
| p1 | | +y | +y | -y | -y | +y | +y | -y | -y | -x | -x | +x | +x | -x | -x | +x | +x | -x | +x | +x | -x | -x | +x | +x | -x | +x | -x | -x | +x | +x | -x | -x | +x |
| p2 | | +y | +y | +y | +y | -y | -y | -y | -y | -x | -x | -x | -x | +x | +x | +x | +x | +y | +y | +y | +y | -y | -y | -y | -y | +x | +x | +x | +x | -x | -x | -x | -x |
| b[b] | | +x | +x | +x | +x | +x | +x | +x | +x | -x | -x | -x | -x | -x | -x | -x | -x | +x | +x | +x | +x | +x | +x | +x | +x | -x | -x | -x | -x | -x | -x | -x | -x |
| Receiver[c] | | +x | -x | -x | +x | -x | +x | +x | -x | +x | -x | -x | +x | -x | +x | +x | -x | -y | +y | +y | -y | +y | -y | -y | +y | +y | -y | -y | +y | -y | +y | +y | -y |
| Receiver[d] | | +x | -x | -x | +x | -x | +x | +x | -x | -x | +x | +x | -x | +x | -x | -x | +x | +y | -y | -y | +y | -y | +y | +y | -y | +y | -y | -y | +y | -y | +y | +y | -y |

[a] Pulse labels are defined in Fig 1a.

[b] Pulses b1, b2, and b3 are identical in the current instance only.

[c,d] The receiver phases for indices 16 through 31 depend upon the relationship between receiver phase and pulse phase in a particular spectrometer. For the exemplary Chemagnetics 300 NMR spectrometer, phases listed for Receiver[c&d] are selected.

*Fig. 2*

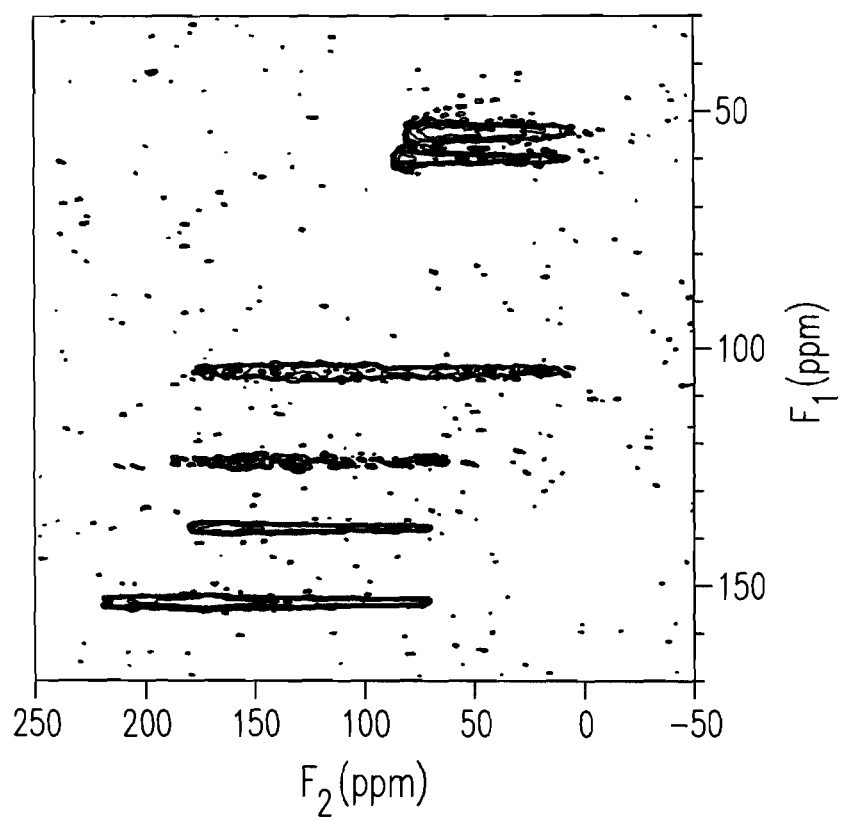
*Fig. 11a*
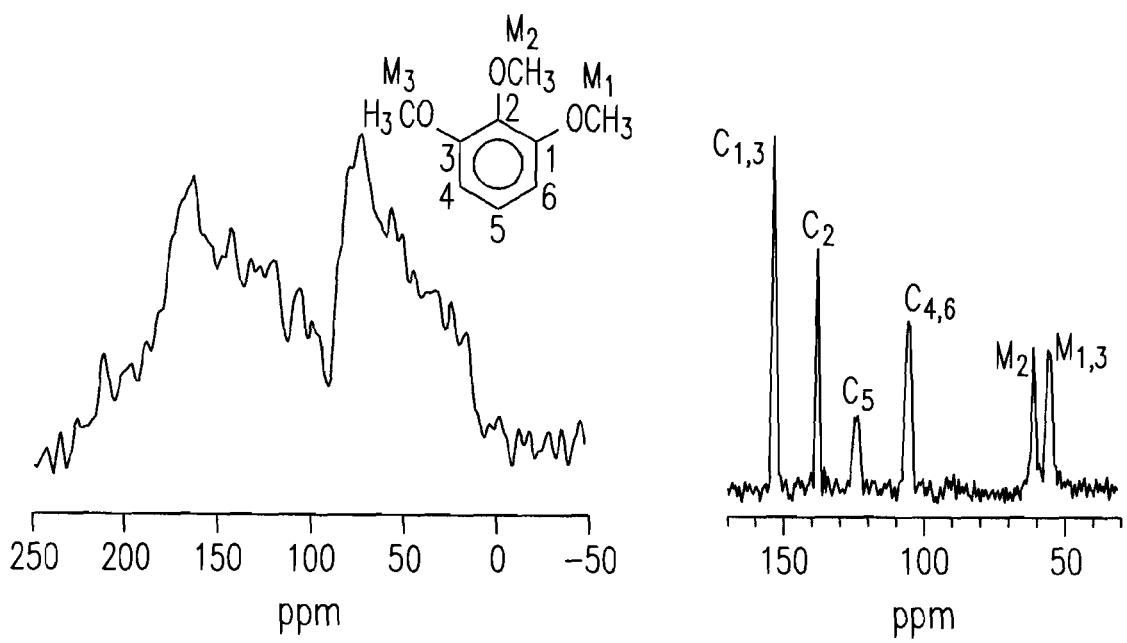
*Fig. 11b*      *Fig. 11c*

DISCRETE MAGIC ANGLE TURNING SYSTEM, APPARATUS, AND PROCESS FOR IN SITU MAGNETIC RESONANCE SPECTROSCOPY AND IMAGING

This invention was made with Government support under Contract DE-AC06-76RLO1830. The Government has certain rights in the invention.

FIELD OF THE INVENTION

The present invention relates to Magnetic Resonance Spectroscopy and/or Imaging, generally. More particularly, the invention relates to a discrete "magic angle" turning (DMAT) system, apparatus, and process for in situ Magnetic Resonance Spectroscopy and/or Imaging.

BACKGROUND OF THE INVENTION

Magic angle spinning (MAS) is one of the most useful experimental techniques known to those of skill in the NMR art. By spinning a sample about an axis inclined at an angle of 54.74° with respect to an externally applied magnetic field ($B_0$), high resolution, high sensitivity isotropic spectra can be obtained that are free from line broadenings induced by various spin interactions. MAS has found widespread application in the study of both solid and semi-solid samples, including, e.g., characterization of organic and inorganic solid materials, biological tissue/cell samples, biofluids, and the like. However, gains obtained in spectral resolution and sensitivity often come with corresponding losses in anisotropic information that, in general, provides more structural information than is derived, e.g., from the isotropic shift. Many two-dimensional (2D) spectroscopic techniques are available in the art to obtain or recover missing or lost anisotropic information. In one illustrative approach, anisotropic line shapes, e.g., spinning sideband (SSB) patterns, can be separated using isotropic chemical shift differences in a 2D spectral plane. Projection along the isotropic dimension yields a high resolution spectrum similar to that obtained from MAS.

However, in practice, true in situ investigations remain difficult or impossible to carry out using conventional MAS and constant fast sample spinning because experimental parameters such as pressure, temperature, and feed compositions must be precisely controlled.

Magic Angle Hopping (MAH) and Magic Angle Turning (MAT) are two techniques known in the art that exhibit advantages that if combinable into one operative system and/or device could have potential to meet requirements for in situ investigations.

In MAH, two successive rapid 120° sample rotations are followed by reverse 240° rotations about the magic angle axis. For times prior to the first 120° rotation, between the two 120° sample rotations, and after the second 120° rotation, magnetization is allowed to precess in the transverse (X-Y) plane. Prior to each 120° rotation, a projection pulse is used to project either cosine or sine components of the magnetization to the main field direction. Since only 240 degree sample rotation is involved, tubes can be introduced or coupled to the sample rotor allowing simultaneous control over pressure, feed compositions, and temperature, at a minimum. However, MAH has proven difficult to implement due to difficulties that include maintaining a rotation axis precisely at the magic angle. Any errors with the angle of rotation can result in line broadening along the isotropic dimension. Consequently, spectral resolution with MAH along the isotropic dimension can be much poorer than that obtained from conventional MAS. Thus, MAH has not found wide acceptance for applications.

In Magic Angle Turning (MAT), samples are continuously rotated and read pulses are synchronized to occur at 120 degrees, or ⅓, of a rotor cycle. Compared with MAH, MAT is easy to perform. First, the magic angle in MAT can be set experimentally with high accuracy due to use of a constant sample spinning speed. Second, read pulses can be spaced accurately at ⅓ of a rotor cycle with the aid of an optical detector or other synchronization device. Because slow sample spinning is employed in MAT, large sample volumes can be used to provide high measurement sensitivity. MAT can also be used successfully in conjunction with Phase-Corrected-Magic-Angle-Turning (PHORMAT) sequences to measure chemical shift tensor principle values for complex molecular structures, and to obtain high resolution $^1H$ NMR metabolite spectra and localized spectra of various organs and tissues in small live animals such as mice. However, despite successes obtained with MAT and PHORMAT, to date, rotations at constant speed have not been attained for in situ investigations where pressure control or tubes for controlling feed compositions become necessary.

Accordingly, new systems, processes, and apparatus are needed that provide the ability to conduct in situ investigations, including study of in situ reactions, where pressure control or tubes for controlling feed compositions are necessary.

SUMMARY OF THE INVENTION

A discrete magic angle turning (DMAT) system, device, and processes are disclosed for in situ Magnetic Resonance Spectroscopy and/or Imaging. DMAT provides advantages seen previously only separately and/or individually in conventional Magic Angle Turning (MAT) and Magic Angle Hopping (MAH) approaches. Spectral resolution obtained with DMAT is similar to MAS and typically superior to MAH.

In one aspect of the invention, a DMAT system for in situ Magnetic Resonance Spectroscopy and/or Imaging includes a DMAT device having a rotor operable for rotation of a sample or a specimen about an axis inclined at an angle of 54°44' relative to a static magnetic field ($B_0$) in a clockwise and/or in an anti-clockwise rotation direction at a constant speed through a preferred rotation angle of greater than about 240 degrees and less than or equal to about 360 degrees, or optionally to an angle greater than or equal to about 360 degrees, wherein the clockwise and the anti-clockwise rotation directions are substantially reverse rotation directions to one another and wherein rotation of the rotor is effected in a pulsed radio frequency magnetic field ($B_1$); a driving assembly operably connected for driving the rotor of the DMAT device; a speed controller operably coupled to the driving assembly providing a speed profile that synchronizes rotation of the sample or specimen at the constant speed to an evolution period of a pulsed RF pulse segment generated by the pulsed radio frequency magnetic field ($B_1$); and wherein spectroscopic data generated during the evolution period of the pulsed RF pulse segment and acquired following rotation of the sample or specimen in at least one of the clockwise or anti-clockwise rotation directions provides for high resolution in situ spectroscopic analysis and/or imaging of the sample or specimen.

In another aspect of the invention, a DMAT device (probe) for in situ Magnetic Resonance Spectroscopy and/or Imaging, includes a rotor for rotation of a sample or a specimen in a clockwise and/or an anti-clockwise rotation direction at a constant speed about an axis inclined at a "magic angle" of 54°44' relative to a static magnetic field ($B_0$) through a rotation angle of greater than about 240 degrees and less than or equal to about 360 degrees, or optionally to an angle greater than equal to about 360 degrees. The clockwise and anti-clockwise rotations are substantially reverse rotation directions to one another. The term "probe" in reference to the DMAT device refers to that part of an NMR spectrometer (e.g., an MAS NMR spectrometer) that accepts a sample or specimen, rotates the sample or specimen, sends specific and/or tuned RF energy into the sample or specimen, and detects, measures, and collects signal data emanating from the sample or specimen, including in situ measurements and data, for analysis of the same. Rotation of the rotor is effected in a pulsed radio frequency magnetic field ($B_1$). A speed controller couples to the DMAT probe, providing a speed profile for rotation of the rotor that synchronizes rotation of the sample or specimen at the constant speed to an evolution period of a pulsed RF pulse segment generated by the pulsed radio frequency magnetic field ($B_1$). Spectroscopic-data generated during the evolution period of the pulsed RF pulse segment is preferably acquired following rotation of the sample or specimen in at least one of the clockwise or anti-clockwise rotation directions, which provides for high resolution in situ spectroscopic analysis and/or imaging of the sample or specimen. Components of the probe include, but are not limited to, e.g., a sample rotor (container) for rotating a sample or specimen, sample RF coil, fixed and variable RF tuning circuitry and/or components, as well as other auxiliary components providing temperature control of the sample or specimen, components, and the like. In another embodiment, an optical detector that includes, e.g., fiber optic fibers and circuitry for indicating position of the rotor and thus the sample or specimen. No limitations are intended. The non-continuous and discrete nature of the probe rotation allows for connecting tubes or feed lines directly to, or into, the sample rotor (container) permitting 1) introduction of reactants or other suitable feed compositions to the sample rotor, 2) introduction of gaseous constituents to the sample rotor, e.g., to control pressure, to purge, or to introduce gaseous components, and 3) extraction of product samples or reaction aliquots, and the like. In various embodiments, tubes or feed lines may be positioned anywhere along the length or width of the sample rotor. In other embodiments, the probe includes a directional (axis) mechanism mounted to the rotor assembly for positioning or adjusting the rotor assembly to a desired angle. In other embodiments, the probe is configured with an optical detection system, a monitoring system, or the like. In an exemplary embodiment, the probe is configured with a computer-controlled monitoring system for collection of sample measurement data. In another embodiment, the DMAT probe is configured with an optical detector or system providing transistor-to-transistor logic pulse sequencing. The sequencing is adapted to trigger corresponding RF pulse sequencing in synchronization with precision markers mounted on the rotor assembly. In yet other embodiments, the period at constant speed for the probe is synchronized to begin at least by the start of the evolution period (i.e., RF pulse segment) and to finish at least by the end of the evolution period before acquiring spectroscopic data.

In another aspect of the invention, a DMAT process for in situ Magnetic Resonance Spectroscopy and/or Imaging, comprises: providing a sample or specimen; rotating the sample or specimen about an axis inclined at an angle of 54°44' relative to a static magnetic field ($B_0$) in a clockwise and/or in an anti-clockwise rotation direction at a constant speed through a rotation angle of greater than about 240 degrees and less than or equal to about 360 degrees, or optionally to an angle greater than equal to about 360 degrees; wherein the clockwise and the anti-clockwise rotation directions are substantially reverse rotation directions to one another; wherein rotating of the sample or specimen is effected in a pulsed radio frequency magnetic field ($B_1$); pulsing the RF magnetic field providing an RF pulse segment; providing a speed profile, wherein rotating of the sample or specimen at the constant speed is synchronized to an evolution period characteristic of the pulse segment generated in conjunction with pulsing of the radio frequency (RF) magnetic field; acquiring spectroscopic data generated from pulsing of the RF magnetic field during the evolution period following rotation of the sample or specimen in at least one of the clockwise and/or the anti-clockwise rotation directions at constant speed; and wherein spectroscopic data acquired during the evolution period from the pulsed RF pulse segment provides for high resolution spectrum for in situ spectroscopic analysis and/or imaging of the sample or specimen. In various embodiments, the process of the invention provides various (RF) pulse sequences necessary to obtain high-quality spectra using back and forth rotations that are typically less than about 360 degrees. In one embodiment, a sample or specimen is rotated clockwise followed by rotation of the sample or specimen in an anticlockwise direction of equal angular distance. Each rotation is through a distance of greater than about 240°, but less than or equal to about 360°. Rotation speed is constant for times related only to the evolution dimension, i.e., the period of the RF pulse sequence or segment. In other embodiments, the evolution period is preceded by an acceleration period and followed by a deceleration period. In other embodiments, spectroscopic data are acquired following the evolution period either a first direction (e.g., clockwise) or second direction (e.g., counterclockwise) or vice versa. In yet other embodiments, the evolution period spectroscopic data are acquired following the evolution period in both a first direction (e.g., clockwise) and second direction (e.g., counterclockwise) or vice versa. In other embodiments, a rotational frequency is selected in the range from about 2 Hz to about 3 Hz; or in the range up to about 40 Hz; or from about 0.01 Hz to about 40 Hz about the magic angle axis; or from about 1 Hz to about 100 Hz. In an exemplary embodiment, the pulse sequence is an HPDEC pulse sequence for decoupling proton signals for $^{13}C$ analysis of a solid. Since sample rotation of less than or equal to about 360 degrees is preferably involved, tubes or feed lines can be inserted into the sample rotor of the NMR probe without plumbing interferences experienced from mechanics associated with continuous sample rotation. The process is envisioned to be useful for in situ investigations, including, e.g., investigations of catalyst reactions under precisely controlled conditions, and investigations of biological fluid systems such as dense cell systems, including those with cells attached to solid surfaces. Further, in situ investigation of fluid-filled objects are of interest, including biological objects (cells, cell aggregates, cell systems, tissues, organs, and the like), live specimens of various sizes and shapes that include live animals and potentially human patients.

In still yet another aspect of the invention, a DMAT process for in situ Magnetic Resonance Spectroscopy and/or Imaging comprises the steps: providing a sample or specimen; rotating the sample or specimen about an axis inclined at an angle of 54°44' relative to a static magnetic field ($B_0$) in a clockwise and/or in an anti-clockwise rotation direction at a constant speed through a rotation angle of greater than about 240 degrees and less than or equal to about 360 degrees, or optionally to an angle greater than about 360 degrees, wherein the clockwise and the anti-clockwise rotation directions are substantially reverse rotation directions to one another and wherein rotating of the sample or specimen is effected in a pulsed radio frequency magnetic field ($B_1$), wherein rotating of the sample or specimen is done in an apparatus performing discrete magic angle turning (DMAT), comprising of at least the following components: (i) a rotor operable for rotation of a sample or a specimen about an axis inclined at an angle of 54°44' relative to a static magnetic field ($B_0$) in a clockwise and/or in an anti-clockwise rotation direction at a constant speed through a rotation angle of greater than about 240 degrees and less than or equal to about 360 degrees and optionally greater than about 360 degrees, wherein the clockwise and the anti-clockwise rotation directions are substantially reverse rotation directions to one another and wherein rotation of the rotor is effected in a pulsed radio frequency magnetic field ($B_1$); (ii) wherein the clockwise and the anti-clockwise rotation directions are substantially reverse rotation directions to one another and wherein rotation of the rotor is effected in a pulsed radio frequency magnetic field ($B_1$); (iii) a driving assembly operably connected for driving the rotor of the DMAT apparatus; (iv) a speed controller operably coupled to the driving assembly providing a speed profile that synchronizes rotation of the sample or specimen at the constant speed to an evolution period of a pulsed RF pulse segment generated by the pulsed radio frequency magnetic field ($B_1$); providing a speed profile, wherein rotating of the sample or specimen at the constant speed is synchronized to an evolution period characteristic of the pulse segment generated in conjunction with pulsing of the radio frequency (RF) magnetic field; pulsing the RF magnetic field providing an RF pulse segment; providing a speed profile, wherein rotating of the sample or specimen at the constant speed is synchronized to an evolution period characteristic of the pulse segment generated in conjunction with pulsing of the radio frequency (RF) magnetic field; acquiring spectroscopic data generated from pulsing of the RF magnetic field during the evolution period following rotation of the sample or specimen in at least one of the clockwise and/or the anti-clockwise rotation directions at constant speed; and wherein spectroscopic data acquired during the evolution period from the pulsed RF pulse segment provides a high resolution spectrum for in situ spectroscopic analysis and/or imaging of the sample or specimen. In various embodiments, correlation between a high resolution peak and a low resolution peak in a two dimension spectral plane provides additional information for analyzing the sample or specimen. In another embodiment, the method employs two or more iterations of rotating of the sample or specimen at constant speed in the clockwise and/or the anti-clockwise rotation directions.

In various embodiments, the DMAT probe is of a modular design, wherein probe components are of variable dimensions which can be adapted for use on small (sub-mm), medium-to-large (tens of cm), and potentially large (>60 cm) fluid and biological objects. In still yet other embodiments, a DMAT probe can be inserted in an external magnetic field and rotated about an axis positioned at an angle of 54°44' (the so-called magic angle) relative to the external magnetic field ($B_0$) at various spinning speeds. In preferred embodiments, spin speeds of less than about 100 Hz are selected. In other embodiments, spin speeds of up to about 40 Hz are selected. In still yet other embodiments, spin speeds are selected in the range from about 0.01 Hz to about 40 Hz, being sufficiently low to prevent damage to structural integrity of an object or animal that can result from centrifugal forces associated with spinning. The novel design provides control over temperature, pressure, flow conditions (e.g., of liquid reagents), and feed compositions permitting in situ investigations. For example, the DMAT probe is adapted to provide in-situ analysis of fluid-based objects, biological objects, cells, cell clusters, cell aggregates, tissues, organs, live animals, solids, as well as mounted forms of each, including combinations thereof. In other embodiments, RF pulse sequences or segments are used, selected from, e.g., PHORMAT, SP-PHORMAT and variations thereof; optionally including high power decoupling (HPDEC), water suppression using CHESS, DANTE, and WET, or the like, and combinations thereof. In other embodiments, the speed profile further includes a smooth acceleration and deceleration period at the beginning and the end of the constant speed period to achieve the constant speed of rotation or to decelerate the speed of rotation down to a static state, respectively, prior to a subsequent rotation in an opposite rotation direction. Alternatively, the speed profile further includes an acceleration period employed prior to initiation of the constant speed period for ramping the speed of rotation in the counterclockwise rotation direction to match the speed selected for the period at constant speed and a deceleration period employed subsequent to the period of constant speed for decreasing the speed of rotation of the sample or specimen to a substantially stopped position prior to a subsequent rotation in the counterclockwise rotation direction.

While the present invention is described herein with reference to the preferred embodiments thereof, it should be understood that the invention is not limited thereto, and various alternatives in form and detail may be made therein without departing from the spirit and scope of the invention. In particular, those skilled in the art will appreciate that exemplary shielding, gradient coil(s), rotor assembly, mounts, and/or other allied components described herein can be of varying dimensions to accommodate variability in sizes, shapes, and dimensions of various specimens, including, e.g., fluid or biological objects (e.g., live animal specimens), as well as varied parameters of the exemplary probe, and/or other allied components (console, optical detection system, monitoring system, etc.) as described herein, or to collect data related to the same. Thus, no limitation in scope is intended by reference to the preferred embodiments herein.

BRIEF DESCRIPTION OF THE DRAWINGS

A more complete appreciation of the invention will be readily obtained by reference to the following description of the accompanying drawings in which like numerals in different figures represent the same structures or elements.

FIG. 2 is a chart showing exemplary pulse phases useful in conjunction with SP-DMAT pulse sequences, according to an embodiment of the process of the invention.

FIG. 11a presents a 2-D contour plot obtained from the $^{13}$C CP-DMAT spectrum of 1,2,3-trimethoxybenzene, according to an embodiment of the process of the invention.

FIG. 11b presents the anisotropic power pattern obtained from the $^{13}$C CP-DMAT spectrum of 1,2,3-trimethoxybenzene of FIG. 11a by summing all the data onto the $F_2$ (anisotropic dimension) axis, according to an embodiment of the process of the invention.

FIG. 11c presents a high resolution isotropic projection obtained from the $^{13}$C CP-DMAT spectrum of 1,2,3-trimethoxybenzene of FIG. 11a by summing all the data onto the $F_1$ (isotropic dimension) axis, according to an embodiment of the process of the invention.

DETAILED DESCRIPTION OF THE INVENTION

Figure 1A:
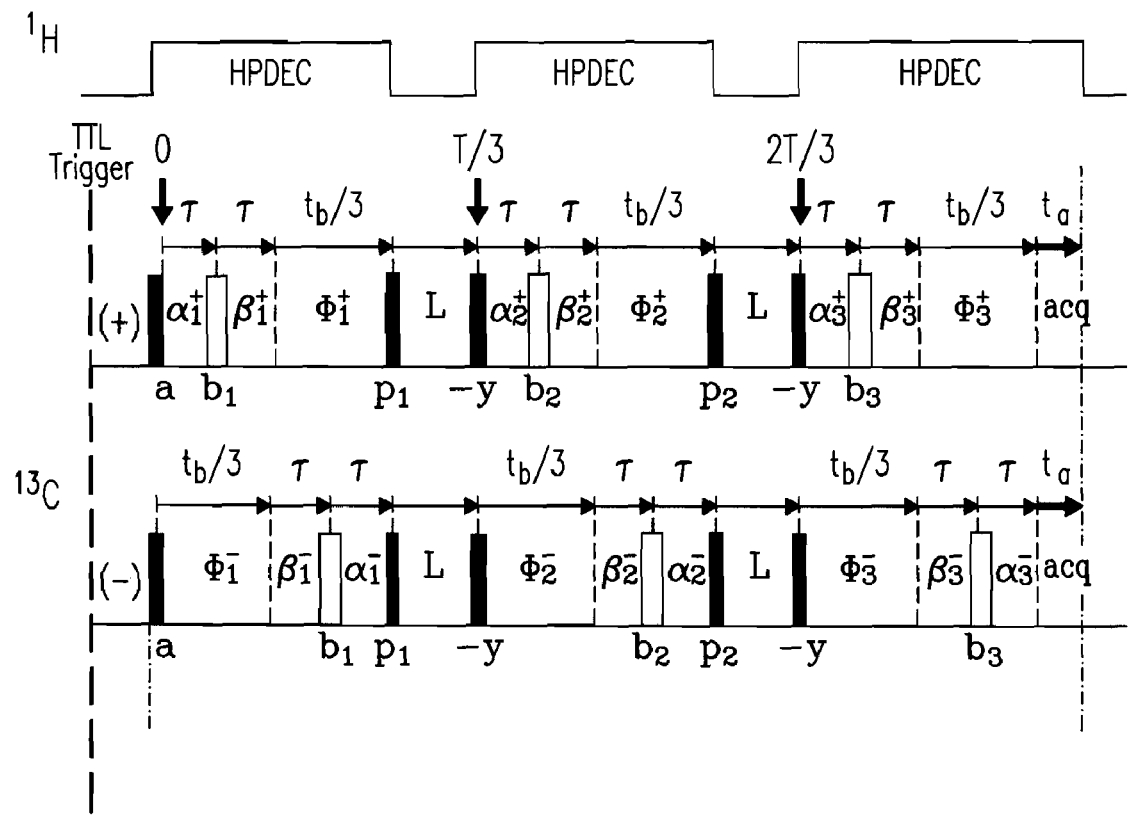
FIG. 1a presents a Non-Cross Polarization variant of a PHORMAT pulse sequence, i.e., SP-DMAT, according to an embodiment of the process of the invention.

While the present invention may be embodied in many different forms, for the purpose of promoting an understanding of the principles of the invention, reference will now be made to embodiments illustrated in the accompanying drawings and specific language will be used to describe the same, in which like numerals in different figures represent the same structures or elements. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

The present invention relates to new Discrete Magic Angle Turning (DMAT) systems, processes, and apparatus suitable for in situ Magnetic Resonance Spectroscopy and/or Imaging, in accordance with various embodiments of the invention. DMAT is a new isotropic-anisotropic shift 2D correlation spectroscopy that incorporates advantages found in both Magic Angle Turning (MAT) and Magic Angle Hopping (MAH). The invention is suitable for use in conjunction with magnetic resonance spectroscopy and/or imaging instruments and finds application in analysis of, e.g., solids, biological objects and specimens, food products, in situ reactions, e.g., catalysis reactions, chemical reactions, and the like, including investigations related to same.

For ease of understanding, the following terms are used herein.

The term "discrete" means rotation that does not proceed continuously or solely in one rotation direction. Discrete magic angle turning systems, processes, and apparatus of the invention thus involve "discrete", or non-continuous rotation, of a sample or specimen.

The term "in-situ" as used herein means "in place", referring to the ability of the system, apparatus, and processes of the instant invention to measure dynamic chemical changes in a sample or specimen in real-time as they occur in the sample rotor, e.g., in response to a reagent, a gas, or other chemical constituent introduced thereto, permitting real-time monitoring, characterization, and/or analysis of a sample and/or specimen. Chemical changes envisioned hereby include, but are not limited to, e.g., metabolic changes, physiologic changes, including chemical products and/or intermediates produced, and reaction changes related to same. No limitations are intended.

The term "sample" as the term is used herein refers to substantially solid objects analyzed in conjunction with the invention. Samples include, but are not limited to, e.g., catalysts, viscous solids, reactants, food stuffs, food products, and the like.

The term "specimen" as used herein refers to samples comprising a substantial amount of a fluid, such as greater than about 50 wt % fluid. Specimens include, but are not limited to, e.g., cells, tissues, organs (e.g., animal and/or human organs), biological samples, live animals, human patients, or the like, including portions thereof mounted to stationery structures, e.g., cells mounted to or grown on glass beads.

The term "evolution period" or "evolution dimension" as used herein means the time segment or period employed in Discrete Magic Angle Turning (DMAT), a two-dimensional (2D) NMR experiment, between the start and end of an RF pulse sequence or segment at a constant rotation speed prior to data acquisition. The evolution period can be effected both in a forward and a reverse direction in concert with speed profiles adapted for generation of same.

The term "Rank-2 Spin Interactions" or "Second-order Spin Interactions" as the terms are used herein refer to second-order polynomial or series expansion terms that characterize specific spin interactions. Second-order spin interactions in DMAT are typically averaged to zero (i.e., "averaged out") to obtained well-resolved spectra for dilute spin components or dilute species present in a sample or specimen. Second-order, or rank-2, spin interactions include, but are not limited to, e.g., dipole-dipole couplings, chemical shift anisotropies, isotropic magnetic susceptibility interactions, and residual homonuclear dipolar interactions present in, e.g., biological fluid samples.

The term "Cross-Polarization (CP)" as used herein refers to a transfer of polarization or magnetization energy to $^{13}$C nuclei in a spectrometer from the magnetization of more sensitive $^1$H nuclei coupled thereto. By using CP, sensitivity of $^{13}$C measurements can be increased. Use of (CP) in PHORMAT spectroscopy is described, e.g., by Hu et al. (in Hu J Z, Wang W, Liu F, Solum M S, Alderman D W, Pugmire R J, Grant D M, 1995. Magic-angle-turning experiments for measuring chemical-shift-tensor principal values in powdered solids. *J Magn Reson* A 113: 210-222.), incorporated herein in its entirety. An exemplary cross-polarization technique described herein is CP-DMAT.

The term "Single-Pulse" (SP), used herein in reference to SP-DMAT pulse sequencing, refers to a non-(CP) variant of single pulse (SP) sequences known to those of skill in the NMR spectroscopic art. Use and application of (SP) pulse sequencing in PHORMAT is described, e.g., by Hu et al. (in Hu J Z, Rommerein D N, Wind R A. 2002a. High resolution $^1$H NMR spectroscopy in rat liver using magic angle turning at a 1 Hz spinning rate. *Magn Reson Med* 47: 829-836.), incorporated herein in its entirety. (SP) can be coupled to DMAT, yielding unique SP-DMAT pulse sequences suitable for use in conjunction with the system, apparatus, and process of the invention. No limitations are intended.

The term "High Power (HP) Decoupling" or (HPDEC) as used herein has its ordinary and customary meaning as will be understood by those of skill in the NMR spectroscopic art. HPDEC is a technique or process used to decouple, or remove the line broadening from $^1$H spin. Use of HPDEC in PHORMAT is described, e.g., by Hu et al. (in Hu J Z, Wang W, Liu F, Solum M S, Alderman D W, Pugmire R J, Grant D M. 1995. Magic-angle-turning experiments for measuring chemical-shift-tensor principal values in powdered solids. *J Magn Reson* A 113: 210-222.), incorporated herein in its entirety.

The invention provides high-resolution spectra in concert with use of magic angle spinning, e.g., for in situ investigations. Samples or specimens are rotated about an axis inclined at an angle of 54°44' relative to a static magnetic field ($B_0$) in a clockwise and/or in an anti-clockwise rotation direction at a constant speed through a rotation angle of greater than about 240 degrees and less than or equal to about 360 degrees, and optionally at an angle greater than or equal to about 360 degrees. Rotation of the sample or specimen is effected in a pulsed radio frequency (RF) magnetic field ($B_1$). Pulsing of the RF magnetic field provides an RF pulse segment. A speed profile is provided wherein rotation of the sample or specimen at constant speed is synchronized to an evolution period characteristic of the pulse segment generated in conjunction with pulsing of the radio frequency (RF) magnetic field. Spectroscopic data generated from pulsing of the RF magnetic field during the evolution period is acquired following rotation of the sample or specimen in at least one of the clockwise and/or the anti-clockwise rotation directions. Spectroscopic data acquired during the evolution period from the pulsed RF pulse segment provides for high resolution spectra for in situ spectroscopic analysis and/or imaging of the sample or specimen. Rotational frequencies are preferably in the range from about 2 Hz to about 3 Hz; or in the range up to about 40 Hz; or from about 0.01 Hz to about 40 Hz about the magic angle axis; or from about 1 Hz to about 100 Hz. Pulse sequences as are known to those of skill in the spectroscopic arts may be employed without limitations. In an illustrative embodiment, an HPDEC pulse sequence is used for decoupling proton signals for $^{13}$C analyses of solids. Rotation speed is maintained at a constant rate at least for times corresponding or related to the evolution dimension. Clockwise and counter-clockwise rotation is repeated and synchronized with a special radio frequency (RF) pulse sequence to produce an isotropic-anisotropic shift 2D correlation spectrum. For any spin-interactions of rank-2, including, e.g., dipole-dipole couplings and chemical shift anisotropies, projection along the isotropic dimension provides a high resolution spectrum. Since sample rotation of less than or equal to about 360 degrees is preferred, constituent tubes or feed lines can be inserted into the sample rotor of the DMAT system and device without interfering with the mechanics of the sample rotation experienced with continuous rotation systems. The novel design described herein permits further control over such conditions as temperature, pressure, flow of fluids and reactants including, e.g., liquids and gases, as well as feed compositions such that true in-situ investigations can be carried out. For example, the methodology is potentially useful, e.g., for in-situ investigation of catalyst reactions under precisely controlled conditions, as well as biological systems such as dense cell systems or cells attached to solid surfaces.

Following are references that describe various features, components suitable for use in conjunction with the present invention. References including papers, publications, patents, or other written materials disclosed herein are hereby incorporated in their entirety herein: U.S. Pat. Nos. 6,653,832; 6,670,811; 6,989,674; U.S. application Ser. No. 11/562,390 filed Nov. 21, 2006; Wind et al. "High resolution $^1$H NMR spectroscopy in organs and tissues using slow magic angle spinning." Magn Reson Med 2001; 46: 213-218; Hu et al. "High Resolution $^1$H NMR Spectroscopy of Metabolically Active Microorganisms Using Non-Destructive Magic Angle Spinning", Spectroscopy 2004; 19: 98-102; Wind et al. "Slow-MAS NMR methods to study metabolic processes in vivo and in vitro," Advances of NMR in Food Science (Engelsen S B, Belton P S, and Jakobsen H J, eds.), Royal Society of Chemistry, Cambridge, 156-165 (2005).

The discrete magic angle turning (DMAT) technique will now be described in reference to FIGS. 1a-1b.

FIG. 1a presents a Non-Cross Polarization (CP) version of a single pulse (SP) excitation PHORMAT (or SP-PHORMAT) pulse sequence. Theory for operation of constant-speed, i.e., the sample is rotating in one direction at a constant speed, PHORMAT sequences is detailed, e.g., by Hu et al. (Hu J Z, Wang W, Liu F, Solum M S, Alderman D W, Pugmire R J, Grant D M. 1995. Magic-angle-turning experiments for measuring chemical-shift-tensor principal values in powdered solids. *J Magn Reson* A 113: 210-222.), incorporated herein in its entirety. DMAT theory is derived from the theory of PHORMAT by realizing, for the first time, that the same theory also works if only the speed corresponding to the evolution segment of the PHORMAT sequence is constant. Timing and phases of pulses are illustrated. In the figure, 90 degree (or $\pi/2$) pulses are represented by black narrow rectangles; 180 degree (or $\pi$) pulses are denoted by cross-hatched rectangles. Projection pulses ($p_1$) and ($p_2$) are labeled. Read-out pulses are synchronized at times (0), (T/3) and (2T/3), where (T) denotes the period of rotation corresponding to the constant speed rotation segment. Phases of the first pulse are changed according to the single pulse version of the experiment (FIG. 2). In the figure, magnetization precesses in the transverse (i.e., X-Y) plane during the periods labeled by total phase accumulation angles $\alpha_1$, $\beta_1$, $\Phi_1$, $\alpha_2$, $\beta_2$, $\Phi_2$, $\alpha_3$, $\beta_3$, and $\Phi_3$, and is along the longitudinal axis during the periods labeled "L". Herein, ($\tau$) is an echo delay time determined by the probe ringdown and receiver recovery time. Function of each ($\pi$) pulse is to negate the phase of the magnetization. Projection pulses labeled ($p_1$) and ($p_2$) project either a cosine or a sine component of magnetization to the external magnetic field direction. During the period labeled (L), the component of magnetization remaining in the transverse plane is destroyed by either dipolar dephasing (e.g., in the case of solids) or by a pulsed field gradient (e.g., in the case of a biological sample). A combined FID for (+) pulse sequences is described, e.g., by Hu et al. (in *J. Magn. Reson A* 113 (1995) 210-222), incorporated herein, by selecting phases of pulses (e.g., as described in reference to in FIG. 2) and adding the 32 individual FIDs (or multiples thereof) together, yielding a combined FID given by the Equation in [3]:

$$F^+ = e^{i((\beta_1^+ + \beta_2^+ + \beta_3^+) - (\alpha_1^+ + \alpha_2^+ + \alpha_3^+) + (\Phi_1^+ + \Phi_2^+ + \Phi_3^+))} F_\alpha(t_\alpha), \quad [3]$$

Here $F_\alpha(t_\alpha)$ corresponds to the FID along the acquisition dimension ($t_2$), which is a powder average of the response obtained from analysis of a solid powder sample. The other phase angles are calculated as follows, using equations [4a]-[6d]:

$$\alpha_1^+ = \int_0^\tau \omega(\gamma(t))dt, \quad [4a]$$

$$\alpha_2^+ = \int_{T/3}^{T/3+\tau} \omega(\gamma(t))dt = \int_0^\tau \omega(\gamma(t+T/3))dt, \quad [4b]$$

$$\alpha_3^+ = \int_{2T/3}^{2T/3+\tau} \omega(\gamma(t))dt = \int_0^\tau \omega(\gamma(t+2T/3))dt, \quad [4c]$$

$$\alpha_1^+ + \alpha_2^+ + \alpha_3^+ = \int_0^\tau [\omega(\gamma(t)) + \omega(\gamma(t+T/3)) + \omega(\gamma(t+2T/3))]dt \quad [4d]$$

$$\beta_1^+ = \int_\tau^{2\tau} \omega(\gamma(t))dt = \int_0^\tau \omega(\gamma(t+\tau))dt, \quad [5a]$$

$$\beta_2^+ = \int_{T/3+\tau}^{T/3+\tau+\tau} \omega(\gamma(t))dt = \int_0^\tau \omega(\gamma(t+\tau+T/3))dt, \quad [5b]$$

$$\beta_3^+ = \int_{2T/3+\tau}^{2T/3+\tau+\tau} \omega(\gamma(t))dt = \int_0^\tau \omega(\gamma(t+\tau+2T/3))dt, \quad [5c]$$

$$\beta_1^+ + \beta_2^+ + \beta_3^+ = \quad [5d]$$
$$\int_0^\tau [\omega(\gamma(t+\tau)) + \omega(\gamma(t+\tau+T/3)) + \omega(\gamma(t+\tau+2T/3))]dt$$

$$\Phi_1^+ = \int_{2\tau}^{2\tau+t_b/3} \omega(\gamma(t))dt = \int_0^{t_b/3} \omega(\gamma(t+2\tau))dt, \quad [6a]$$

$$\Phi_2^+ = \int_{T/3+2\tau}^{T/3+2\tau+t_b/3} \omega(\gamma(t))dt = \int_0^{t_b/3} \omega(\gamma(t+2\tau+T/3))dt, \quad [6b]$$

$$\Phi_3^+ = \int_{2T/3+2\tau}^{2T/3+2\tau+t_b/3} \omega(\gamma(t))dt = \int_0^\tau \omega(\gamma(t+2\tau+2T/3))dt, \quad [6c]$$

$$\Phi_1^+ + \Phi_2^+ + \Phi_3^+ = \quad [6d]$$
$$\int_0^\tau [\omega(\gamma(t+2\tau)) + \omega(\gamma(t+2\tau+T/3)) + \omega(\gamma(t+2\tau+2T/3))]dt$$

Here (T) represents the period of rotation at constant speed. Angles $\gamma(x)$, $\gamma(x+T/3)$ and $\gamma(x+2T/3)$ denote rotor positions equally spaced at 120 degrees around the circle (i.e., 360 degrees) of rotation during the period (T), where (x)=(t), (t+$\tau$) and (t+2$\tau$), respectively. When the rotation axis is inclined at the magic angle with respect to the external field, three rotor positions put the static magnetic field in three mutually perpendicular directions with respect to the sample or specimen. For spins that are subject to second-rank interactions, including, e.g., chemical shift anisotropy, magnetic susceptibility interactions, and weak dipolar coupling, resonance frequencies at these mutually perpendicular field directions average to the isotropic value of the interaction, as given by Equation [7]:

$$\omega(\gamma(x)) + \omega(\gamma(x+T/3)) + \omega(\gamma(x+2T/3)) = 3\omega_{iso}, \quad [7]$$

Here $\omega_{iso}$ is the resonance angular frequency of the isotropic shift. Equation [3] becomes:

$$F^+ = e^{i((\beta_1^+ + \beta_2^+ + \beta_3^+) - (\alpha_1^+ + \alpha_2^+ + \alpha_3^+) + (\Phi_1^+ + \Phi_2^+ + \Phi_3^+))} F_\alpha(t_\alpha) \quad [8]$$

$$= e^{i(3\omega_{iso}\tau - 3\omega_{iso}\tau + 3\omega_{iso}t_b/3)} F_\alpha(t_\alpha)$$

-continued $$= e^{i\omega_{iso}t_b} F_\alpha(t_\alpha)$$

Similarly, for the (–) pulse sequence presented in FIG. 1a, the expression in [9] is obtained:

$$F^- = e^{-i\omega_{iso}t_b} F_\alpha(t_\alpha) \quad [9]$$

Cosine and sine components of the FID along the evolution dimension are obtained by adding and subtracting $F^-$ and $F^+$, e.g., as described by Hu et al. (*J. Magn. Reson A* 113 (1995) 210-222), to obtain a hyper-complex 2D FID. A 2D Fourier transformation generates a pure 2D absorption spectrum, where projection along the isotropic dimension yields a high resolution isotropic spectrum, while projection along the acquisition dimension provides an anisotropic pattern. In the DMAT approach, derivations from Equations [4] and [9] only require a constant speed of rotation during the evolution time (or evolution dimension) of the experiment, i.e., during the time period from "0" to [2T/3+2$\tau$+$t_b$/3] illustrated in FIG. 1a. By forcing the time period at constant rotation to a value of [$\geq$2T/3+2$\tau$+($t_b$)$_{max}$/3], where ($t_b$)$_{max}$ is a maximum evolution time used in the 2D experiment, an isotropic-anisotropic 2D spectrum is obtained.

In one embodiment, a SP-DMAT pulse sequence described herein includes a PHORMAT pulse sequence without $^1$H HPDEC while keeping the (+) and (–) sequences the same. The instant embodiment would be useful for observing any kind of spin-½ nuclei where the dipolar coupling between the observed nucleus and the other abundant nuclei can be ignored. In another embodiment, a SP-DMAT pulse sequence described herein includes a water suppressed $^1$H PHORMAT sequence for metabolic profiling of biological tissues and live animals. Sequences of this type have been detailed, e.g., by Hu et al. [*Magn. Reson. Med.* 47, 829-836 (2002)] and Wind et al. [*Magn. Reson. Med.* 50, 1113-1119 (2003)], incorporated herein in their entirety. In another embodiment, replacing the pulse labeled (a) in FIG. 1a with a cross-polarization (CP) segment, a CP-DMAT pulse sequence can be constructed. Such an experiment is similar to that described, e.g., by Hu et al. [*J. Magn. Reson.*, A 113, 210-222 (1995)], suitable for measuring chemical-shift tensor values in powdered solids.

Figure 1B:
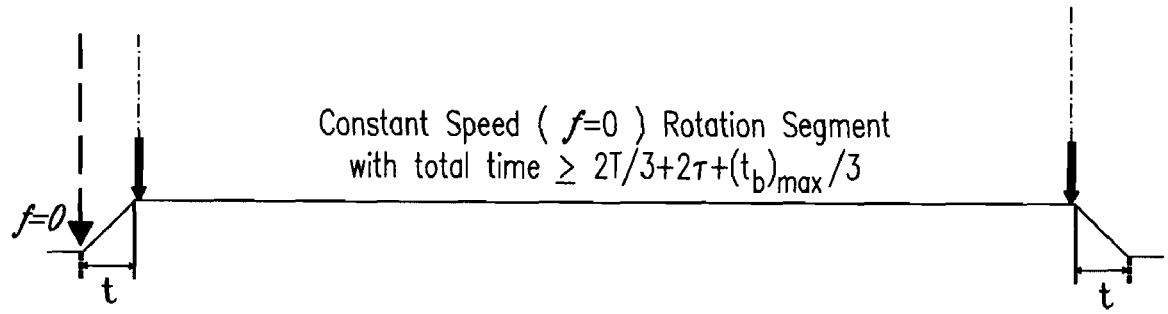
FIG. 1b is a depiction of a speed profile corresponding to the pulse sequence of FIG. 1a for sample rotation, according to an embodiment of the process of the invention.

FIG. 1b depicts an exemplary speed profile for conducting rotation of a sample or specimen using the DMAT approach, according to an embodiment of the process of the invention. In the figure, the experiment is conducted in conjunction with the exemplary PHORMAT sequence discussed in reference to FIG. 1a. Here, rotation speed is specified in units of Hz. The sample or specimen is stationary initially (i.e., f=0). Rotation is preferably accelerated at a constant acceleration rate (a), given in units of (degree/s$^2$) during time period (t) such that at the end of (t), speed of rotation is given by Equation [10]:

$$f_0 = a \times t/360 \quad [10]$$

Following acceleration, the sample or specimen is rotated at a constant speed over a time (evolution) period defined by equation [11]:

$$[\geq 2T/3 + 2t + (t_b)_{max}/3] \quad [11]$$

Here, (T) corresponds to the period of rotation at constant speed; ($t_b$)$_{max}$ is a maximum evolution time used in the evolution period of the 2D experiment. At the end of the rotation period at constant speed, rotation is decelerated to a value of (f=0) over a time period of (t) using an acceleration having a value equal to (–a). A recycle delay time follows the deceleration period of the experiment. Data acquisition time ($t_2$) begins immediately at the end of the last time period, ($t_b/3$). Period ($t_2$) can be done completely during the rotation period at constant speed, but is not limited thereto. In an alternate embodiment, for example, a portion of ($t_2$) can be effected during the rotation period at constant speed and the remainder can extend into the deceleration time (t). During the recycle delay, rotation is precisely reversed.

Figure 4:
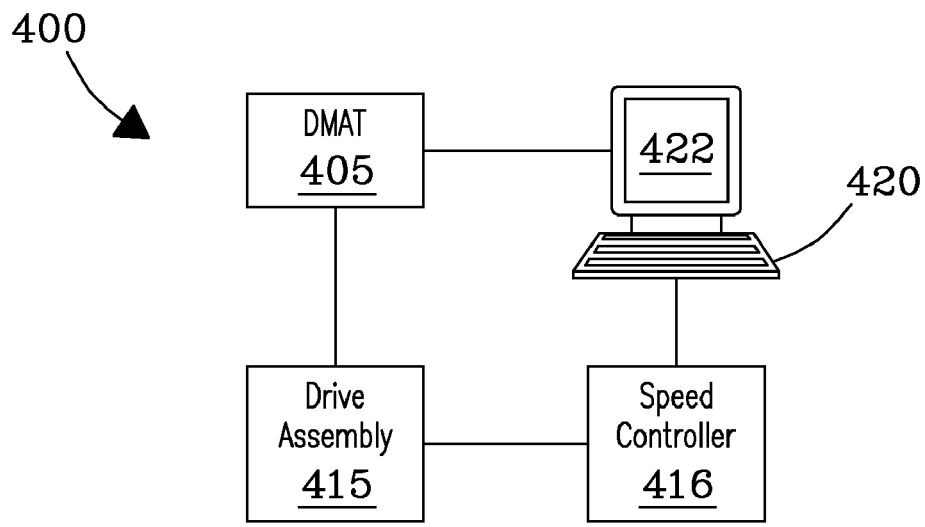
FIG. 4 illustrates a DMAT system, according to an embodiment of the invention.

A driving assembly, described further herein in reference to FIG. 4, includes a stepper or servo motor equipped with a digital encoder that provides control over rotation of a sample or specimen introduced to a sample rotor, including monitoring of the rotation position of the stepper motor and thus of the sample rotor. In a preferred embodiment, the digital encoder has a finite resolution (N) of, e.g., 2000 counts evenly distributed over a 360 degree sample rotation. Counts per degree of rotation are given by the ratio (N/360); total number of counts (d) during the acceleration period (t) is then given by Equation [12]:

$$d = (a \times t^2/2) \times (N/360) \quad [12]$$

By selecting desired values of (d) and ($f_0$), one can find solutions for terms (a) and (t) using Equations [10] and [12]. The driving assembly couples to the DMAT system and apparatus of the invention, as described further herein.

FIG. 2 presents exemplary pulse phases used in concert with the DMAT, pulse sequence, and speed profile described hereinabove in reference to FIGS. 1a-1b. The pulse sequence given in FIG. 1a along with the pulse phases detailed in FIG. 2 are programmed, e.g., into a computer used in conjunction with an NMR spectrometer and suitable spectrometer software, e.g., as will be provided with the instrument or as will be understood by those of skill in the art. The speed profile can be similarly programmed or downloaded into the memory of a speed controller described further herein that determines the speed of rotation of the sample or specimen. When the DMAT experiment is initiated, the NMR spectrometer sends a transistor-to-transistor (TTL) trigger signal to the speed controller. The speed controller initiates rotation according to the programmed speed profile, e.g., as given in FIG. 1b. An exemplary flow chart of events including that for synchronization of the pulse sequence and the speed profile, are presented in FIG. 3.

Figure 3:
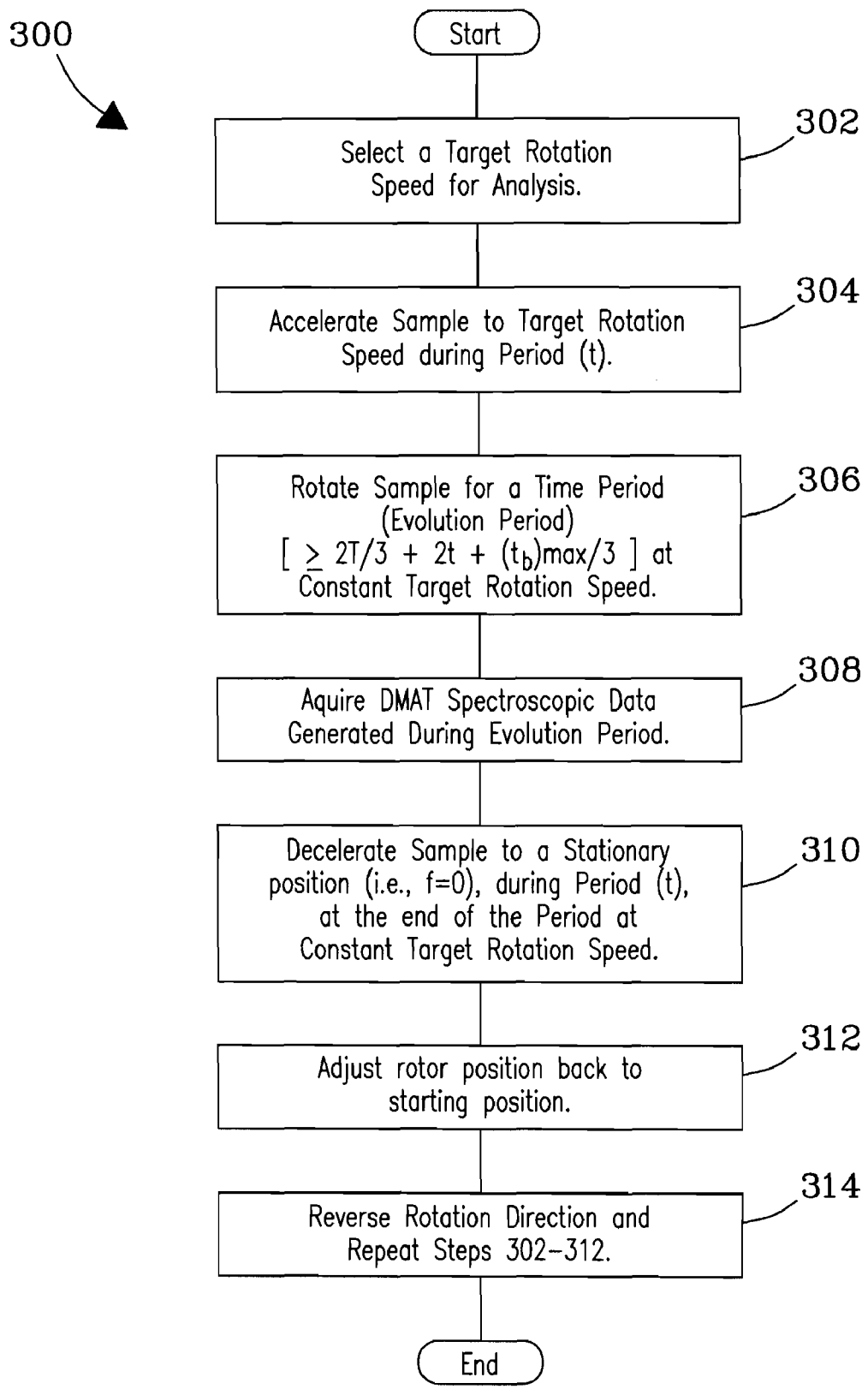
FIG. 3 is a flow chart showing exemplary steps for conducting a 2D-DMAT experiment, according to an embodiment of the process of the invention.

FIG. 3 illustrates an exemplary process 300 showing exemplary steps for use of a table of exemplary phase pulses illustrated in FIG. 2, according to one embodiment of the invention. START. In one step 302, a target rotation speed is selected suitable for DMAT analysis of a sample or specimen. Rotation speeds are preferably selected in the range from about 0.01 Hz to about 40 Hz. More preferably, rotation speeds are selected in the range from about 0.5 Hz to about 10 Hz. Most preferably, rotation speeds are selected in the range from about 1 Hz to about 5 Hz. In another step 304, the sample or specimen is accelerated in the sample rotor at a constant rate during a period (t) beginning from a rotation speed ($f_0$) of zero (i.e., $f_0=0$) at a stationary rotor position to the selected (target) rotation speed (e.g., 4 Hz). An exemplary value for period (t) is 100 ms, but is not limited. During time period (t), the sample rotor is rotated in a first rotation direction (e.g., clockwise) by the rotor assembly a rotation distance of, e.g., about 10 degrees to about 30 degrees, but is not limited. Speed of rotation proceeds in that same time period from zero up to, e.g., 4 Hz, but is again not limited thereto. In another step 306, the sample or specimen is rotated for a time (evolution) period defined by equation [11] at a constant rotation speed at the target value. During the evolution period, any selected sequence of pulses is initiated and fully executed. In a preferred embodiment, shortly (e.g., 5 ms) after the reaching the desired stable rotation speed, a first pulse (e.g., labeled (a) in FIG. 1a) is pulsed, followed by pulsing of remaining pulses in the programmed pulse sequence until at least the beginning of a data acquisition period ($t_a$), and more preferably until the end of the data acquisition period ($t_a$). During implementation of the pulse sequence at the constant rotation speed reached in step 306, a sample in the sample rotor is rotated by the rotor assembly in a first rotation direction preferably through a rotation angle of greater than or equal to about 240 degrees but less than about 300 degrees. Alternatively, rotation angle may be selected in the range from about 240 degrees to about 360 degrees. Rotation angle may be optionally selected in the range from about 240 degrees to any value beyond 360 degrees. In another step 308, spectroscopic data generated during the evolution period at the target rotation speed from the DMAT experiment using the sequence of pulses is acquired. Time period for acquisition of spectroscopic data is preferably from the beginning of period ($t_a$) to the end thereof. During time period (t), the sample rotor is rotated by the rotor assembly through a rotation angle of, e.g., about 10 degrees to about 30 degrees, but is not limited. In another step 310, at the end of the rotation period at the constant target rotation speed, the sample container is decelerated during a period (t) of, e.g., 100 ms, decelerating to a stationary position (i.e., where $f_0=0$). In another step 312, the rotor assembly is positioned again at its selected starting position. In another step 314, a new direction of rotation is selected, e.g., in a counterclockwise direction, over a time period that again traverses the evolution period (FIG. 1b) previously described. Steps 302-312 are then repeated. END.

In one embodiment, the sequence of pulses is effected during the first rotation direction only (e.g., in a clockwise rotation direction), followed by a period of data collection. In another embodiment, a sequence of pulses is executed in a first rotation direction and also in a second direction (i.e., the reverse of), that taken in the first rotation direction. During the period when direction of rotation of the sample or specimen is reversed, the entire sequence of pulses is also reversed, following which data are again acquired. In the instant embodiment, a time factor saving of about 2 for data acquisition is achieved. However, no time factor advantage is observed if, e.g., spin-lattice relaxation time (T1) is longer than the period of sample rotation corresponding to the constant speed rotation, since any recycle delay period, determined by time needed for magnetization to relax back to its thermal equilibrium state, must be comparable to the value of (T1). In yet other embodiments, multiple sequences of pulses can be run in concert with selected directions of rotation. In general, for each evolution time increment, ($t_b$), in FIG. 1a, a full cycle of pulses is preferably of 32 increments (as illustrated in FIG. 2), or multiples thereof, e.g., 64 (2×), 96 (3×), etc. Further, as will be appreciated by those of skill in the art, change in rotation direction of the sample container in the rotor assembly (and thus of a sample or specimen) can undergo any number of iterations or cycles. Thus, no limitations are intended.

DESCRIPTION OF A DMAT SYSTEM OF A PREFERRED EMBODIMENT

FIG. 4 is a schematic illustrating a Discrete Magic Angle Turning (DMAT) system 400 suitable for spectroscopy and/or imaging, e.g., in situ spectroscopy and/or imaging, according to a preferred embodiment of the invention. System 400 includes a Discrete Magic Angle Turning (DMAT) probe 405 of a magnetic or nuclear magnetic resonance imaging type capable of discrete sample rotation about the magic angle axis; a drive assembly 415; a speed controller 416 operatively coupled to a computer 420, e.g., for operation thereof, and/or a display 422 for displaying and viewing speed profiles selected for rotation of a sample or specimen. Speed controller 416, in conjunction with the stepper motor therein, propels drive assembly 415 via a speed profile programmed therein, which is executed preferably by computer 420, providing simultaneous control of the speed and rotation of the sample or specimen. In the instant embodiment, speed controller 416 (e.g., a model DMC-1414 computer programmable speed controller) available commercially (Galil Motion Control, Inc., Rocklin Calif., USA) is an encased, self-contained device that provides multiple and various interfaces, including, e.g., spectrometer interconnects, trigger interconnects, computer interconnects for interfacing or coupling to a standard computer 420, which further couples including standard display devices, electrical, power, and associated couplings, and the like as will be understood by those of skill in the art. Speed controller 416 provides precise speed control and rotation profiles effecting rotation of the sample or specimen. All instrument components and configurations as will be contemplated by those of skill in the art in view of the disclosure are within the scope of the invention.

Discrete Magic Angle Turning (DMAT) Probe

Figure 5:
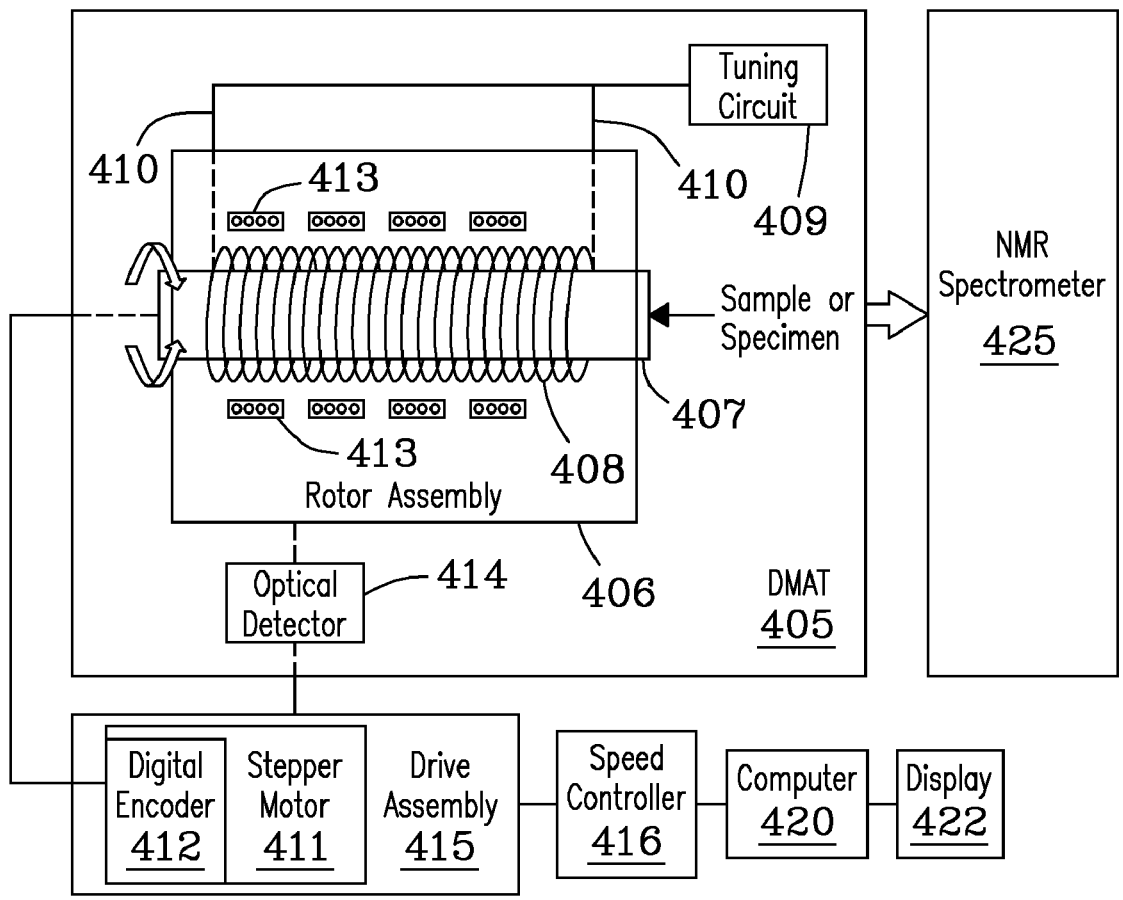
FIG. 5 illustrates an expanded view of a DMAT probe device, according to an embodiment of the invention.

FIG. 5 illustrates an expanded view of DMAT probe 405, the probe being useful in conjunction with an NMR spectrometer 425 for spectroscopy and imaging, e.g., in situ spectroscopy and imaging. In the figure, DMAT probe 405 includes a rotor assembly 406 for rotating a sample therein. Rotor assembly 406 operates in conjunction with sample rotor (container) 407 for containing a sample or specimen introduced thereto for analysis. The sample rotor (container) is made from materials transparent to RF and/or magnetic energy, including, e.g., ceramics, glasses, polymers, and like materials. In the preferred embodiment, the sample rotor (container) is preferably made of a ceramic material that includes a capillary entry point for introduction of feed lines to the sample rotor permitting sample loading and introduction of constituents, including, e.g., reagents, fluids, gases (e.g., purge, flow, and/or respiratory gases), and the like, including combinations thereof, and/or for removing same therefrom. Shape of sample rotor 407 is not limited provided the sample rotor inserts into tuning coil 408 such that the sample or specimen is within the magnetic field generated thereby. In a preferred embodiment, the sample rotor (container) is a 7.5 mm zirconia ceramic rotor sleeve (7.5 mm O.D. and 6 mm I.D.) available commercially (Varian-Chemagnetics, Inc., Palo. Alto, Calif., USA). In the instant embodiment, the DMAT sample rotor 407 is introduced to rotor assembly 406 with two ends open. Glass wool or an equivalent packing material may be inserted a distance into both ends of the sample rotor (container) to both contain and secure a sample (e.g., a powdered sample) introduced thereto for NMR experiments. In other embodiments, alternative and/or additional components may be used for securing the rotor, including samples or specimens therein, within the rotor assembly, including, but not limited to, e.g., end spacers (e.g., polyimide spacers sold commercially under the tradename Vespel®, DuPont, 1-800-441-7515 or 1-302-774-1000, USA), end caps, screws, nuts (UpChurch Scientific, Oak Harbor, Wash., USA), and other allied components. In another embodiment, sample container 407 is a capillary tube secured within rotor assembly 406 using tightly fitting screw nuts known in the art. Sample rotor (container) 407 inserts into tuning coil 408. In one embodiment, tuning coil 408 is, e.g., a 5-turn solenoid coil, but is not limited thereto. The coil couples electrically via leads 410 to RF tuning circuit 409 for charging RF tuning capacitors (FIG. 7) generating the ($B_1$) magnetic fields at various and multiple magnetic field strengths, about which the sample or specimen is rotated at the magic angle.

Rotor assembly 406 is preferably configured with air bearings 413 for suspending sample rotor (container) 407. The air bearings couple to a regulated gas supply, which precisely controls and maintains the rotation axis for the sample rotor.

Drive assembly 415 includes a stepper motor 411 preferably equipped with a digital encoder 412 (e.g., a model ME2130-1988 PM Servo Motor, Cleveland Motion Control, Billerica, Mass., USA). Encoder 412 establishes the number of increments or steps of resolution (e.g., N=2000 increments) in the rotor cycle effected by stepper motor 411. Rotor cycle resolution is not limited. Stepper motor 411 described further herein couples to DMAT probe 405, providing suitable rotation of a sample or specimen introduced to sample rotor 407 and into rotor assembly 406.

Speed controller 416 couples operatively to, and propels, drive assembly 415 in conjunction with a speed profile programmed therein, providing precise speed and rotation profiles effecting simultaneous control of both speed and rotation of the sample or specimen. Speed profiles are executed preferably in conjunction with a computer 420 which can be further coupled to a display 422 or equivalent viewing device.

An optical detector 414, e.g., an LED fiber optic detector (e.g., a combined transmitter/receiver Fiber optic detector), available commercially (Newark Electronics, Chicago Ill., USA), or other synchronization device, couples operatively to rotor assembly 406, providing suitable TTL signal outputs and logic for monitoring speed of the rotor and synchronizing speed of rotation with DMAT pulse sequencing. Detector 414 synchronizes RF pulse sequencing in conjunction with precision markers located on sample rotor 407. For example, read pulses illustrated in FIG. 1*a* can be accurately spaced at selected positions (e.g., at 0, T/3 and 2T/3) of a rotor cycle in conjunction with use of optical detector 414 or an equivalent synchronization device.

Probe 405 and its associated components, can be operated, monitored, and/or controlled, e.g., in conjunction with a computer 420, or like control device. No limitations are intended. All configurations and components and as will be contemplated by those of skill in the art in view of the disclosure are within the scope of the invention.

Figure 6A:
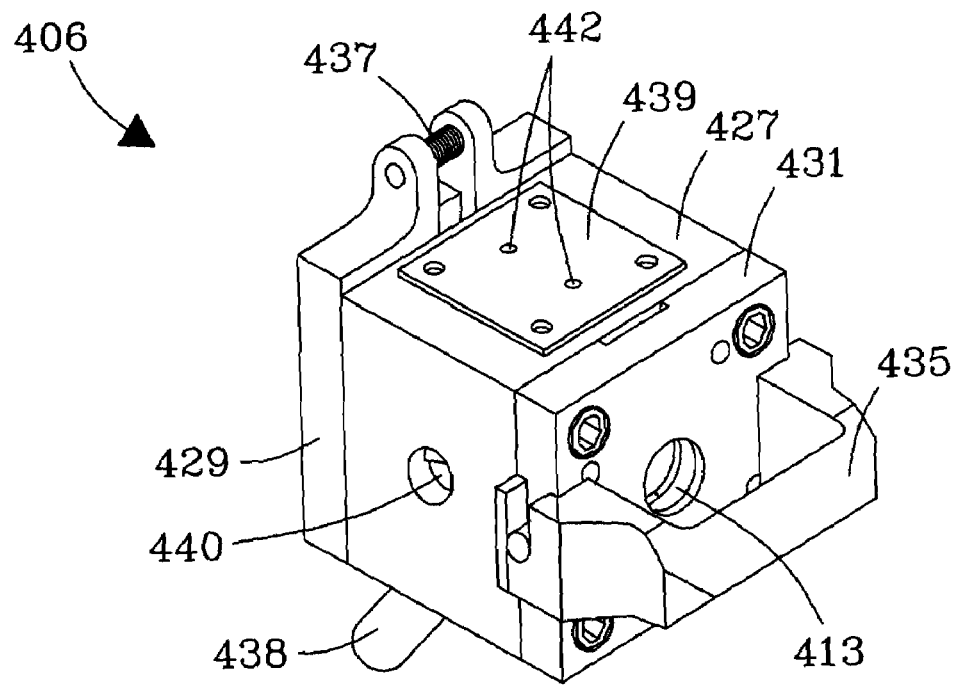
FIGS. 6a-6b illustrate external views of a rotor assembly of a DMAT probe device, for DMAT operation and MAS mode operation, respectively, according to different embodiments of the invention.

FIG. 6*a* illustrates an external view of rotor assembly 406, for operation in DMAT mode, according to an embodiment of the invention. In the figure, rotor assembly 406 includes: a rotor housing 427 comprising of a front face plate 429 and a rear face plate 431; a DMAT sample clip 435 provides quick assembly and disassembly of rotor assembly components, including locking of the sample rotor into the rotor assembly and the rotor pulley (described further in reference to FIG. 7) into place. Clip 435 ensures a precisely controlled rotation axis for turning of the sample or specimen in the rotor, reducing signal inhomogeneity. Front face plate 429 further includes a magic angle pivot pin 437, an attachment point for the magic angle adjustor (FIG. 7). In the figure, a sample coil plate 439 mounted to the exterior of the rotor housing permits mounting and attaching of the RF tuning coil (FIG. 5) inside the rotor assembly. Leads (FIG. 5) from the tuning coil exit the rotor housing through apertures 442 in coil plate 439, connecting electrically to the RF tuning circuit (FIG. 5). In the instant embodiment, the sample rotor is loaded into the tuning coil (FIG. 5) through rear face plate 431, but is not limited. In the figure, air bearings 413 that provide suspension of the sample rotor (container) during rotation in the rotor assembly can be seen through rear face plate 431. Gas inlet 438 provides for introduction of a dry, inert [i.e., a variable temperature (VT)] gas for heating and/or regulating temperature of the sample within the rotor and the interior space of the rotor assembly surrounding the sample rotor. Rotor housing 427 further includes two gas inlets 440 (one of which is shown) located on opposite sides of the housing, providing 1) a supply gas for operation of air bearings 413 in the rotor assembly and 2) a supply gas (drive gas) for spinning the rotor in magic angle spinning (MAS) mode in conjunction with a stator device, described further in reference to FIG. 6b. As will be understood by those of skill in the art, configuration of components described herein with reference to rotor assembly 406 is not limited thereto. All configurations as will be contemplated by those of skill in the art in view of the disclosure are within the scope of the invention.

Figure 6B:
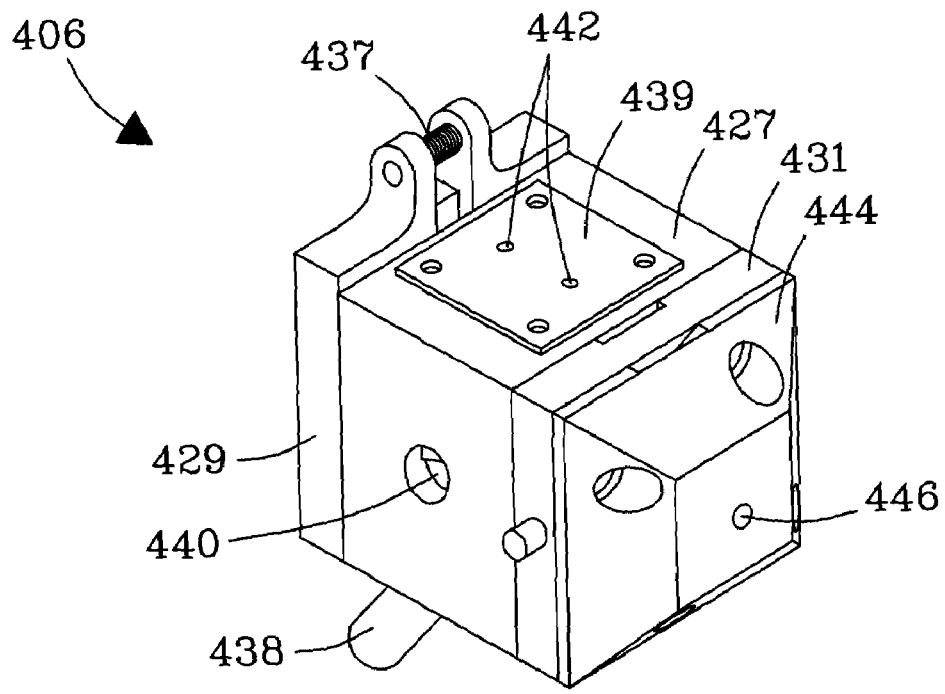
Figure 7:
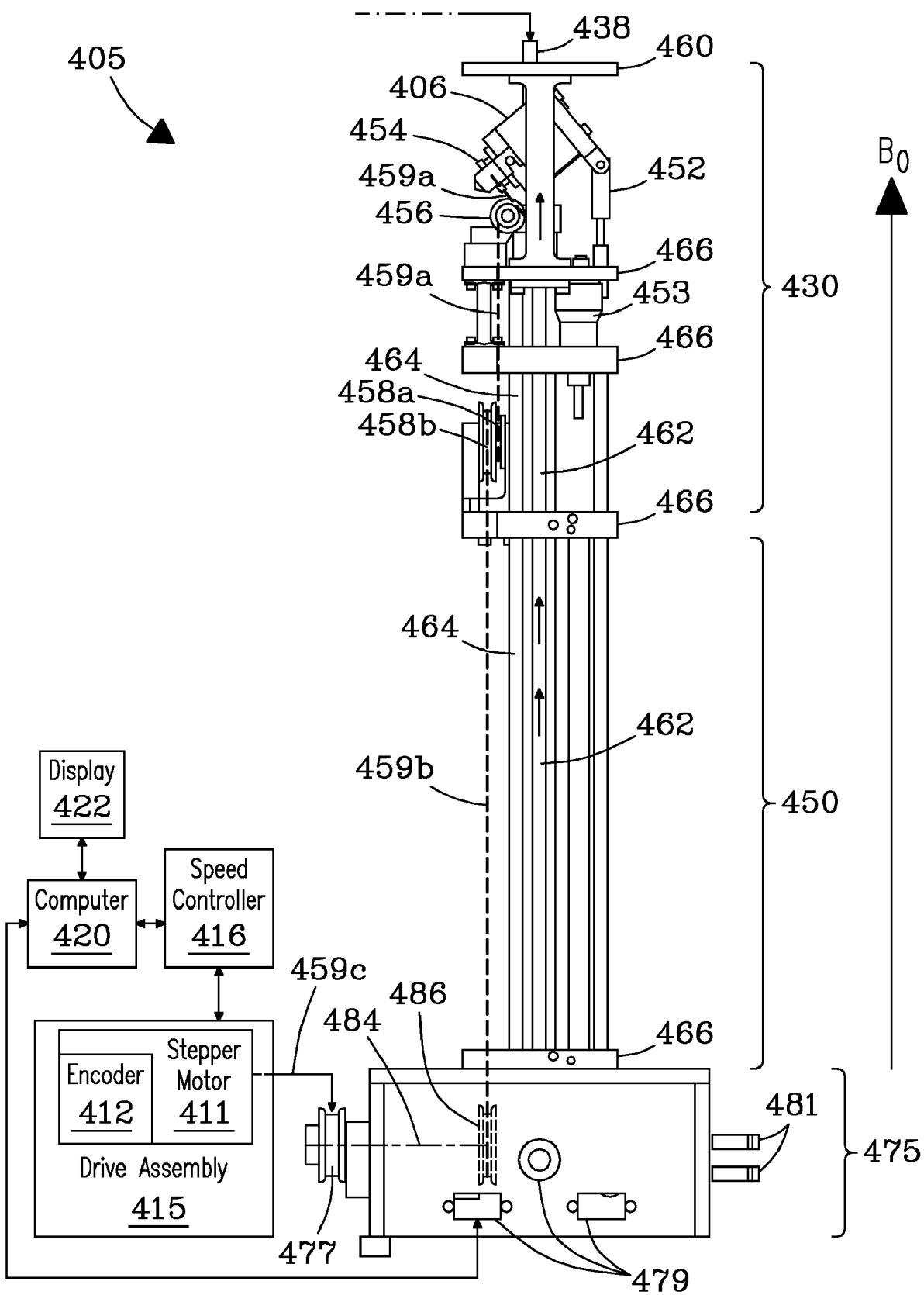
FIG. 7 illustrates an isotopic view of a complete DMAT probe device, according to an embodiment of the invention.

FIG. 6b provides an external view of rotor assembly 406, configured for operation in magic angle spinning (MAS) mode. In MAS mode, a conventional high speed MAS rotor of a pencil type (drive tip) spin design (Varian, Palo Alto, Calif., USA) is inserted in the rotor assembly, permitting DMAT probe 405 to act as a typical MAS probe at sample spinning rates of up to about 4 kHz. The magic angle adjustor (described further in reference to FIG. 7), attaches to magic angle pivot pin 437, permitting the magic angle to be set with a high degree of accuracy. In MAS mode, the magic angle is set and adjusted using, e.g., the FID of KBr as will be known by those of skill in the art. MAS attachment plate 444 mounts to rear face plate 431 after mounting of the MAS rotor and a stator device (not shown) positioned at the rear of the MAS rotor that provides drive gas for spinning of the rotor in the rotor assembly. The stator, machined in-house from a high-grade plastic [e.g., a polyimide polymer sold commercially under the tradename Vespel® (DuPont, 1-800-441-7515 or 1-302-774-1000, USA) includes (e.g., 6) gas vents or outlets that direct drive gas to the MAS rotor for spinning the rotor in the rotor assembly. The stator is anchored into MAS attachment plate 440 via stator seat 446. A conduit (not shown) extending from the drive gas inlet (described in reference to FIG. 6a) to MAS attachment plate 444 supplies drive gas to the stator device. After setting the magic angle, the high speed MAS module is removed and the quick release clip (FIG. 6a) is mounted for DMAT mode operation.

FIG. 7 illustrates a complete DMAT probe 405, according to a preferred embodiment of the apparatus of the invention. In the figure, probe 405 includes a top portion 430, a mid portion 450, and a base portion 475, described further hereafter.

Top portion 430 includes rotor assembly 406 (described previously in reference to FIG. 5 and FIGS. 6a-6b); a magic angle adjustor 452; tuning capacitors 453 coupled to the tuning coil and tuning circuit (FIG. 5); rotor pulley 454, rotor turning pulleys 456; drive pulleys 458a and 458b; and top section (top) plate 460 for introduction of variable temperature (VT) gas supply inlets and outlets, and/or associated fixtures, e.g., reagent, composition, and/or feed source and supply lines. No limitations are intended. Magic angle adjustor 452 attaches to the magic angle pivot pin (FIG. 6a and FIG. 6b) on the rotor assembly and inserts into the base of one of section (supporting) plates 466. The magic angle adjustor further includes both a course adjustment (e.g., a 8-32 pitch turn screw, McMaster-Carr, Los Angeles, Calif., USA) and a fine adjustment (e.g., a 4-40 pitch turn screw, McMaster-Carr, Los Angeles, Calif., USA) coupled operatively that provide approximately a 100-pitch adjustment for setting the magic angle with a high degree of accuracy. Pulleys 454, 456, 458a, and 458b are operatively coupled via drive belts (e.g., 459a and 459b) of appropriate size (Sterling Instrument, Stock Drive Products, Division of Designatronics, Inc., New Hyde Park, N.Y., USA). Pulley 458b further couples operatively to a pulley in base portion 475 described further herein. Pressurized gases, e.g., for operation of rotor assembly 406 are provided through gas conduit 462 to a gas inlet (FIG. 6a and FIG. 6b) located, e.g., at the base of the rotor assembly, but is not limited thereto. Optical fiber for operation of the optical detector (FIG. 5) is channeled through optical conduit 464 and provided through one of several additional section (supporting) plates 466.

Mid portion 450 includes additional and/or suitable lengths of both gas conduit 462 and optical conduit 464, supplying gases for operation of DMAT probe 405 and fiber optic cable for operation of optical detector 414 in conjunction with TTL sequencing, respectively.

Base portion 475 of instant DMAT probe 405 includes interconnects 479 (e.g., electrical interconnects) for interfacing to computer 420, display 422, power sources, and/or devices described herein. Base portion 475 further couples operatively to speed controller 416 and driving assembly 415 described further hereafter. Drive assembly 415 comprises a stepper motor 411 equipped with a digital encoder 412 (e.g., a model ME2130-1988 PM Servo Motor, Cleveland Motion Control, Billerica, Mass., USA). Encoder 412 has a rotor cycle resolution, e.g., of N=2000, but is not limited thereto. Stepper motor 411 couples via a pulley thereon (not shown) and a drive belt 459c (e.g., ~30 inch, anti-slip timing or drive belt, Stock Drive Products/Sterling Instrument, New Hyde Park, N.Y., USA) to input pulley 477 located on base portion 475. Pulley 477 links via an axel shaft 484 to pulley 486 located internal to the base portion. Pulley 486 couples operatively via drive belt 459b (Stock Drive Products/Sterling Instrument, New Hyde Park, N.Y., USA) to pulley 458b in top portion 425, providing rotation of a sample or specimen introduced to the rotor of the rotor assembly. Pulley 486 is preferably of a size or dimension equal to that of pulley 458b such that the rotation profile for each is identical. Similarly, pulley 477 in base portion 475 is preferably of an identical dimension to that of stepper motor 411 such that speed and rotation profile for each is identical, thereby synchronizing turning of the sample or specimen in rotor assembly 406. The person of skill in the art will appreciate that while drive belts and pulleys are described in conjunction with the instant embodiment, positioning, operation, and configuration is not limited. Further, components of the instant probe described in reference to the preferred embodiment are not limited. No limitations are intended.

Probe 405 is configured for use, and/or preferably interfaced to a computer 420 for automating, controlling, and acquiring measurement and test data. In a preferred embodiment, computer 420 operates in conjunction with operation software as will be understood and adapted by those of skill in the art for 1) setting rotational frequency of rotor assembly 406; 2) controlling and monitoring acceleration/deceleration, speed and direction of rotation, and/or other associated control aspects; 3) controlling and monitoring of RF pulse sequencing and triggering (e.g., RF, TTL, etc.); 4) automating collection of measurement data and/or measurement functions/capabilities; and 5) performing analyses. In one aspect, for example, executable code for running speed controller 416 and its associated speed profiles is compiled and saved to computer 420, and subsequently downloaded and stored, e.g., in volatile memory to speed controller 416. Code listed herein is exemplary of codes suitable for executing and running speed profiles, as described previously, e.g., with reference to FIG. 1b, thereby initiating and effecting speed and rotation control of the sample or specimen. Speed controller 416 receives a trigger signal, e.g., a transistor-to-transistor logic (TTL) trigger signal sent out from the pulse sequence, e.g., as illustrated in FIG. 1a, from a spectrometer, including, e.g., an NMR or MRI spectrometer effecting motion of probe 405. Once controller 416 receives a trigger signal, the speed and rotation profile programmed to speed controller 416 is initiated and executed, providing operation of drive assembly 415, including the stepper motor configured therewith, providing rotation of the sample or specimen.

Base portion 475 further includes gas source connects 481 (i.e., inlets and outlets) that provide pressurized gases, e.g., for operation of the air bearings (FIG. 5) that provide for suspension and rotation of the sample rotor; for purging, e.g., of the sample rotor prior to analysis of a sample; for temperature control, e.g., via introduction of variably heated or cooled temperature (i.e., VT) control gases. Gas sourcing and interfacing as described herein is but illustrative of many like configurations, and should not be considered limiting. For example, additional components may be further coupled via interconnects, e.g., tachometer interconnects, and spectrometer interconnects integrated therewith, providing for measurement and collection, e.g., of signal data, as will be understood by those of skill in the art. All interconnects, circuitry, interfaces, and/or feed sources, including equivalents thereof, as will be contemplated by those of skill in the art are within the spirit and scope of the disclosure.

Size of the probe including components thereof may also be increased as will be understood by those of skill in the art for analysis of various sized objects, samples, specimens, and the like. As described herein, probe 405 may be configured with additional components, e.g., a compressor coupled to rotor assembly 406 via tubing, e.g., to supply air to a live animal located within the rotor while probe 405 is in operation. In another embodiment, the rotor may be configured as a catalyst reactor with suitable reagent flows, and temperature and pressure controls for in situ studies of catalysts and catalyst reactions. In another embodiment, the rotor may be configured as a bioreactor in conjunction with necessary control elements such as temperature, nutrient supplies, pressure controls, and the like for in situ detection and monitoring of biochemical processes associated with cells and like cellular systems. No limitations are intended by the disclosure of the instant embodiments. All configurations as will be considered by those of skill in the art in view of the disclosure are encompassed hereby.

Mechanism for Changing Direction of Rotation Axis from Rotation about the MAS to Rotation about an Axis Perpendicular to the Main Field Direction Mechanism for changing direction of rotation of the rotor positioned in the rotor assembly about an axis at the magic angle to that perpendicular to the main magnetic field direction according to the DMAT process described herein is achieved using pulleys and driving or timing belts described previously herein.

In one embodiment, rotor pulley 454 (sample rotation pulley) is preferably of a high performance plastic, e.g., a polyimide polymer known commercially as Vespel® (DuPont, 1-800-441-7515 or 1-302-774-1000, USA). The shaft of the rotor pulley inserts into the rotor sleeve (e.g., a Zirconia ceramic 7.5 mm O.D. with 6 mm I.D., available commercially, Varian, Palo Alto, Calif., USA). To achieve the required tight fit, the shaft of pulley 454 is pre-cooled in liquid nitrogen for about two minutes immediately prior to inserting into the rotor sleeve, which subsequently expands to a gas-tight fit in the rotor sleeve, anchoring the rotor pulley for turning of sample rotor 407 in rotor assembly 406. The sample or specimen is loaded at room temperature into the sample rotor followed by insertion of end plugs (e.g., glass wool) or end caps (not shown) into the sample rotor, securing the sample or specimen therein. Depending on the type of sample, specimen, or application, end plugs and/or end caps may be loosely fitting or tightly fitting. No limitations are intended. DMAT (sample) rotor 407 is then inserted into rotor assembly 406. A threaded endcap introduced at the fore of the DMAT rotor permits introduction of flow gases, liquids (e.g., alcohols), other constituents and/or reagents to the sample rotor. At the rear of the rotor where DMAT rotor pulley 454 attaches, a gas or liquid outlet is provided for removing flow gases, liquids, or other constituents and/or reagents from the sample rotor, which is directed through a filter, e.g., activated charcoal filter, and exhausted to house vacuum in conjunction with a vacuum pump. No limitations are intended.

PULSE SEQUENCING

PHORMAT and Single-pulse PHORMAT (SP-PHORMAT) pulse sequences described herein are exemplary of pulse sequences suitable for use in conjunction with DMAT, according to various embodiments of the invention. PHORMAT is based on a Magic Angle Hopping (MAH) approach detailed by Bax et al. [J. Magn. Reson. 1983; 52: 147] whereby a sample is hopped over angles of 120° about an axis at the magic angle. Prior to each hop, RF storage pulses are applied to orient the magnetization parallel to the external magnetic field ($B_0$) during consecutive hopping periods. Before, in-between, and after two hops, magnetization is allowed to dephase in the transverse (X-Y) plane for a variable evolution time. With a proper phase cycling of the RF pulses and the receiver phases, the MAH experiment produces a conventional 2-dimensional (2D) isotropic-anisotropic correlation spectrum, wherein the isotropic line widths are free from the anisotropy broadening.

Use of the MAT sequences and associated variations, described, e.g., by Gan Z. [J. Am. Chem. Soc. 1992; 114: 8307-8309], Hu et al. [Solid State NMR 3, 181-197 (1994)], Hu et al., [J. Magn. Reson. A113, 210-222 (1995)], Hu et al. [J. Magn. Reson. 163, 149-162 (2003)], and Wind et al. [Magn. Reson. Med. 55, 41-49 (2006)], considered a variant of MAH, may also be used in conjunction with DMAT, according to yet other embodiments of the invention. Here, a sample is rotated slowly and continuously instead of hopped, and the identical effect of 120° hopping is achieved in a preferred mode by synchronizing pulses at about ⅓ of the rotor period.

All pulse sequences as will be contemplated by those of skill in the NMR spectroscopic arts in view of the disclosure are encompassed hereby. No limitations are intended.

FREQUENCY OF ROTATION

Frequency of rotation of the probe, e.g., for in-situ analysis by the method of DMAT, is preferably done at a frequency selected in the range from about 0.5 Hz to about 10 Hz. More particularly, frequency of rotation is selected in the range from about 0.01 Hz to about 100 Hz. In other embodiments, frequency of rotation is selected up to about 40 Hz. Most particularly, frequency of rotation is selected in the range from about 0.01 Hz to about 40 Hz. What rotation frequency to select is based on the spin-lattice relaxation time ($T_1$) and the performance of the DMAT probe. For example, if the ($T_1$)

time is long (e.g., of a seconds duration), a sample spinning rate corresponding to the constant rotation period as slow as about 1 s or less is preferred since the probe device would be most stable. If the ($T_1$) time is short, e.g., ~200 ms or less, a rotation speed of more than 5 Hz is preferred to reduce loss of signal during the experiment.

PROCESS FOR 2-D DMAT

Figure 8:
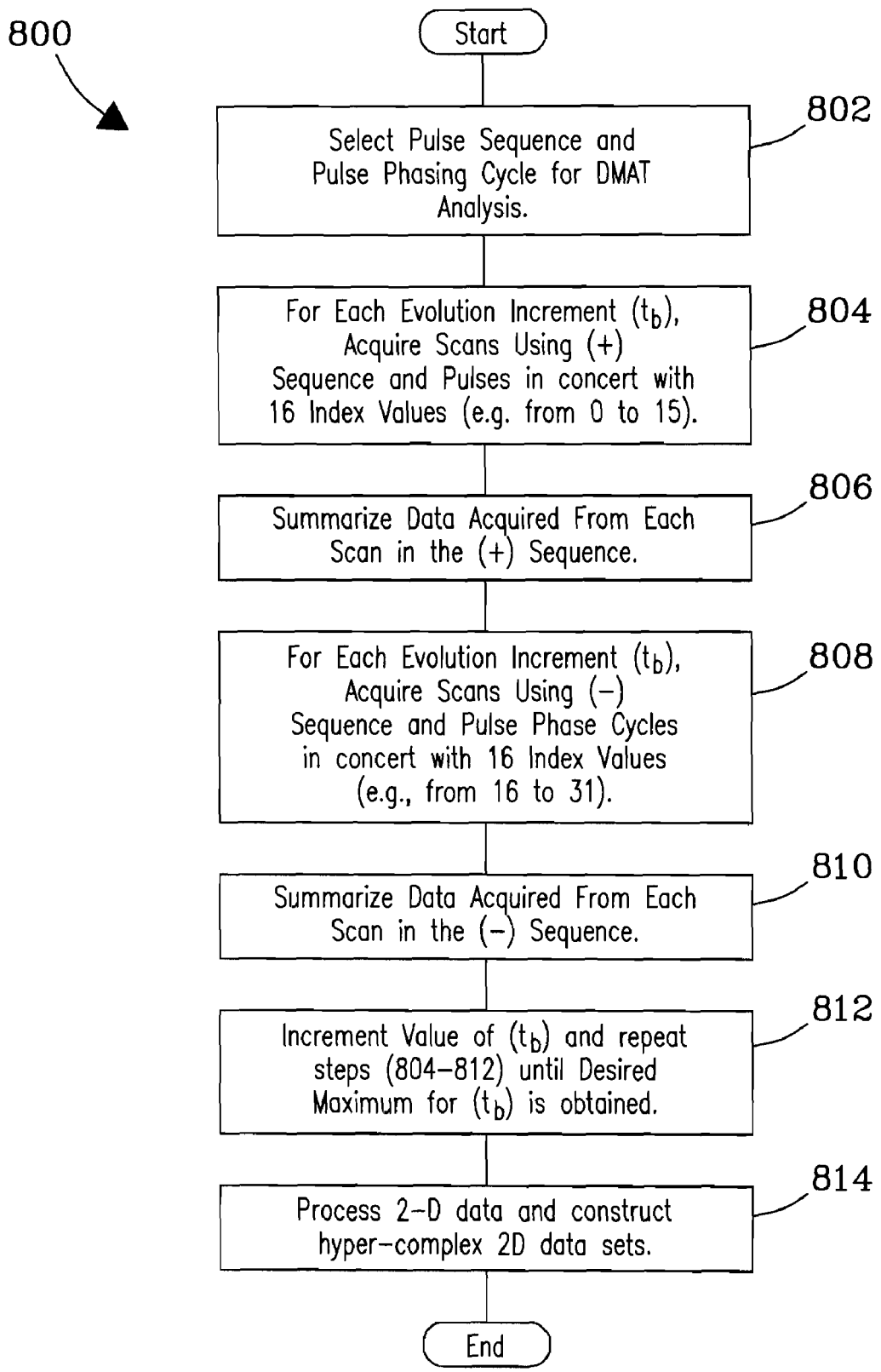
FIG. 8 is a flow chart showing exemplary steps for conducting a DMAT experiment, according to another embodiment of the process of the invention.

FIG. 8 illustrates an exemplary process 800 for conducting a 2-D DMAT experiment, e.g., for generating 2-D spectra, according to an embodiment of the process of the invention. START. In one step 802, a DMAT experiment is configured, including, e.g., selection of a pulse sequence, rotation speed profile and pulse phases as illustrated in FIGS. 1a-1b and FIG. 2, which is initiated and implemented, e.g., according to process steps detailed in FIG. 3. In another step 804, for each evolution time ($t_b$) illustrated in FIG. 1a, scans are acquired in conjunction with a selected pulse sequence [e.g., a (+) sequence of FIG. 1a] and pulse phases (e.g., as illustrated in FIG. 2) for each increment ($t_b$) selected for the evolution period in the first rotation direction using a first set of selected index values (e.g., from 0 to 15). In the instant example, sixteen scans are acquired, but are not limited thereto. In another step 806, data acquired for each scan in the selected pulse sequence are summarized and/or compiled, e.g., in a computer or programmable memory device. In another step 808, scans are acquired in conjunction with a selected pulse sequence [e.g., a (−) sequence of FIG. 1a] and pulse phases (e.g., as illustrated in FIG. 2) for each increment ($t_b$) selected for the evolution period in the second rotation direction using a second set of selected index values (e.g., from 16 to 31). In the instant example, sixteen scans are again acquired, but are not limited thereto. In another step 810, data acquired for each scan are again summarized and/or compiled in a computer or programmable memory device. Data acquisition is interleaved between the (+) and (−) pulse sequences illustrated in FIG. 1a for each value of ($t_b$). In another step 812, value of ($t_b$) is incremented and steps 804-812 are repeated until a desired maximum for ($t_b$) is obtained. In another step 814, acquired 2D data are subsequently processed, e.g., as detailed by Hu et al. in [J. Magn. Reson. A 105, 82-87 (1993)], providing hyper-complex 2D data sets. END.

Following are examples that provide a further understanding of the invention, its various aspects, and capabilities.

EXAMPLE 1

Figure 9A:
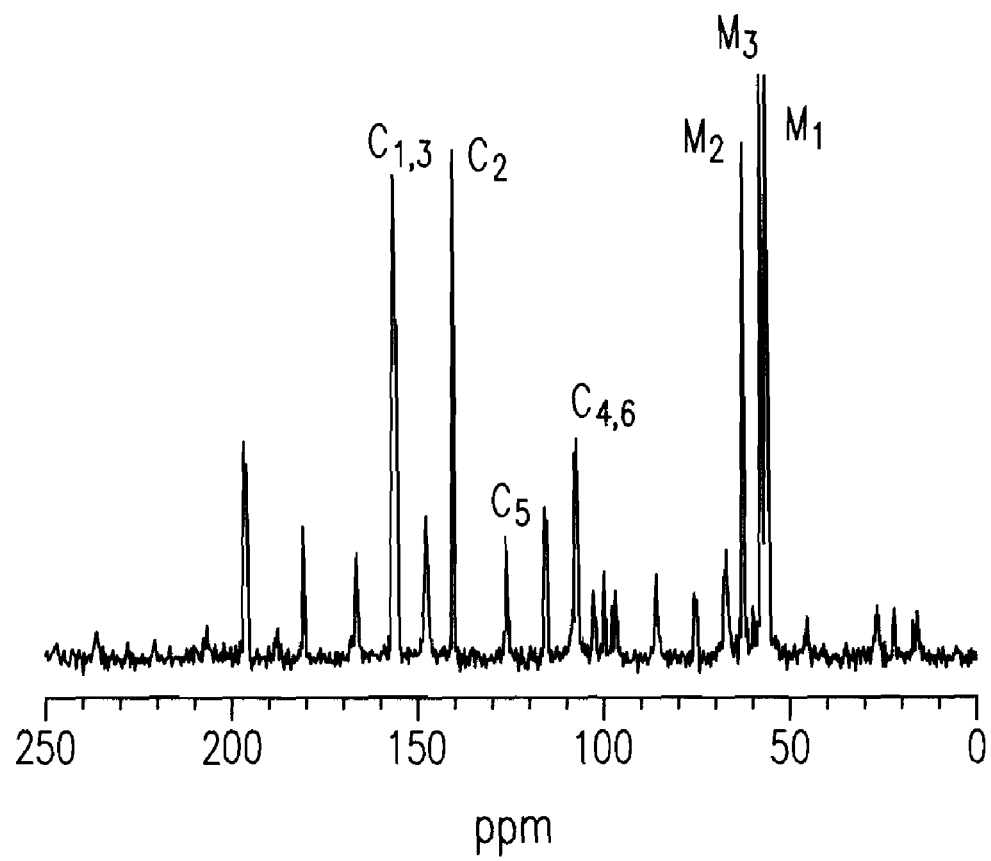
FIGS. 9a-9b present $^{13}$C CP/MAS spectra of 1,2,3-trimethoxybenzene obtained using a DMAT device, according to an embodiment of the process of the invention.
Figure 9B:
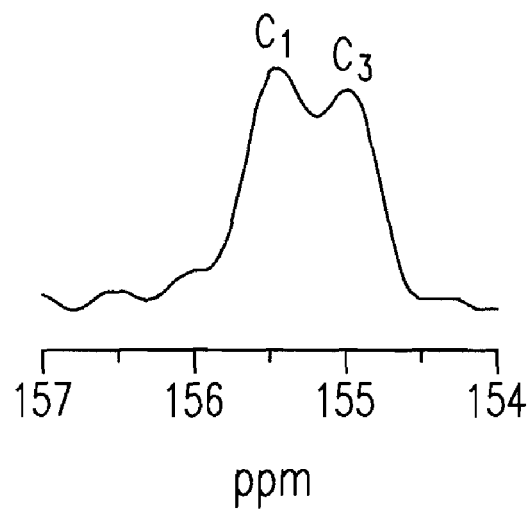

Samples of 1,2,3-trimethoxybenzene (1,2,3-TMB) (Aldrich Chemical Co., Milwaukee, Wis., USA) were analyzed with a Chemagnetics 300 MHz Infinity (NMR) spectrometer (Varian, Palo Alto, Calif., USA) in conjunction with a DMAT probe of the invention using CP-MAS pulse sequencing. A high speed magic angle spinning (i.e., MAS) module (FIG. 6b) was mounted to the rotor assembly of the DMAT probe. The magic angle was set, adjusted using KBr. Sample spinning rate was 3.05 kHz, but is not limited. Larmor frequencies of 75.438 MHz and 299.9835 MHz, for $^{13}C$ and $^1H$, respectively, were used. FIG. 9a presents a $^{13}C$ CP-MAS spectrum, obtained using a cross-polarization (CP) time of 2 ms, 8 accumulation numbers, and a recycle delay time of 5 sec. The 90 degree (i.e., $\pi/2$) pulse width for the initial $^1H$ was 6.5 µs. The $^1H$ field strengths were about 38.5 kHz and 30 kHz during the (CP) and high-power (HP) decoupling (HPDEC) periods, respectively. Unlabeled peaks in the figure correspond to spinning sidebands (SSBs) from the various labeled isotropic peaks. Peaks for carbons $C_1$ and $C_3$ in FIG. 9a are partially resolved, as are $M_1$ and $M_3$ peaks corresponding to methoxy moieties in the chemical structure of the compound. FIG. 9b shows expanded peaks for carbons $C_1$ and $C_3$, which differ by 0.46 ppm. Peaks $C_4$ and $C_6$ have potential to be resolved using an increased decoupling strength. Spectral resolution obtained with the DMAT probe correlated well with a reference MAS probe at the same magnetic field strength, indicating the magic angle in the present experiment was well tuned using the high speed module of the DMAT probe.

EXAMPLE 2

Adamantane, or tricyclo [$3.3.1.1^{3,7}$] (←Jian . . . is the exponent correct?) decane having chemical formula ($C_{10}H_{16}$), is a common $^{13}C$ NMR chemical reference standard. Adamantane (Aldrich Chemical Co., Milwaukee, Wis., USA) was analyzed using a Chemagnetics 300 MHz Infinity (NMR) spectrometer (Varian, Palo Alto, Calif., USA) in conjunction with the DMAT probe of the invention using 2D SP-DMAT pulse sequencing, e.g., as described previously with reference to FIG. 1a. Acceleration time (t) was about 110 ms, proceeding from an acceleration value of zero initially to about 2 Hz, the target rotation speed. A first pulse labeled (a) was triggered 4 ms after constant speed was reached, leaving a maximum of [500 ms−2T/3−114 ms=52.6 ms] for segments of the sequence (i.e., $2\tau+t_b/3$). At a typical value of, e.g., ($\tau$=100 µs), the maximum value of ($t_b/3$) is about 52.4 ms, resulting in a maximum evolution time for the evolution dimension of about 157.5 ms. Recycle delay time was 3s. Free-induction decay in the acquisition dimension ($t_2$) contained 256 complex points, which were transformed to spectra having a spectral width of 10 kHz. 2D data were collected using 200 ($t_b$) steps each incremented at 500 µs, corresponding to a maximum evolution time of 100 ms and an evolution spectral width of 2 kHz. 2D data sets were acquired with the (+) and the (−) DMAT pulse sequences (see FIG. 1a) using 64 scans at each ($t_b$) value, for a total measuring time of about 11 hours. Hyper-complex 2D data sets were constructed, e.g., as detailed by Hu et al. (in J. Magn. Reson A 113 (1995) 210-222), using a macro driven program developed in-house on the Chemagnetics Infinity Spectrometer. Results are presented in FIGS. 10a-10c, discussed hereafter.

Figure 10A:
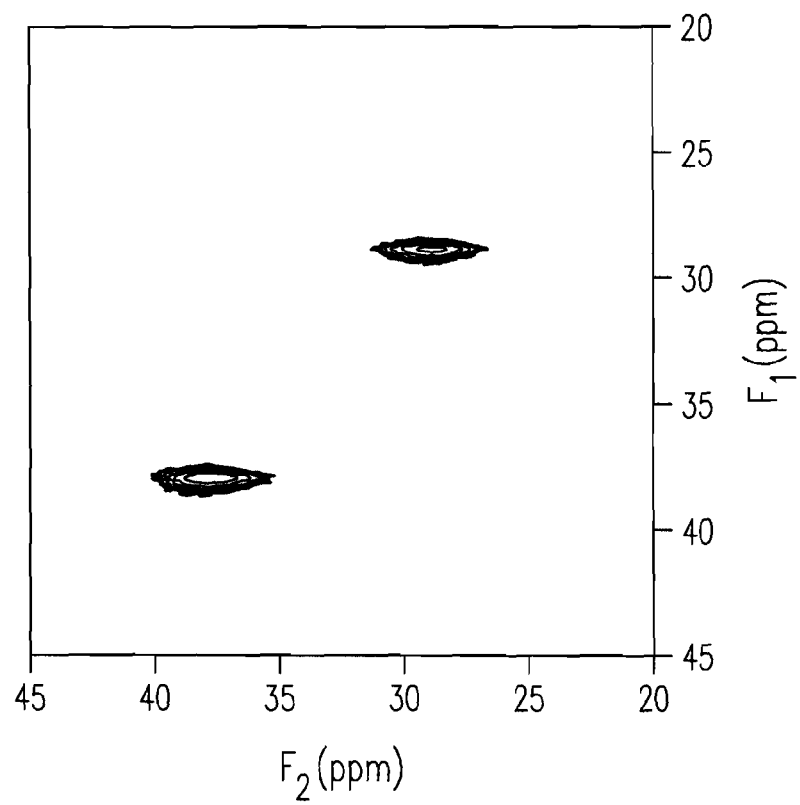
FIG. 10a presents an isotropic-anisotropic 2-D correlation spectrum from a $^{13}$C NMR spectrum of adamantine obtained using a SP-DMAT pulse sequence, according to an embodiment of the process of the invention.
Figure 10B:
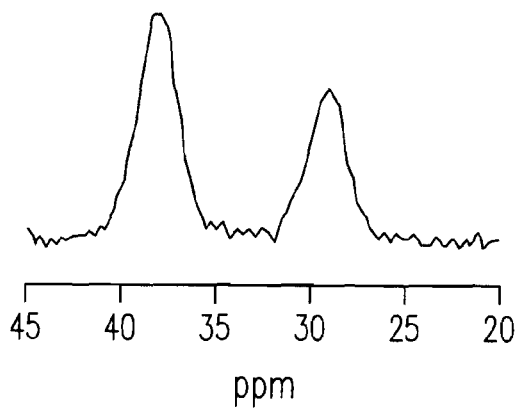
FIG. 10b presents an anisotropic projection to the acquisition dimension ($F_2$ axis) obtained from the spectrum of FIG. 10a, according to an embodiment of the process of the invention.
Figure 10C:
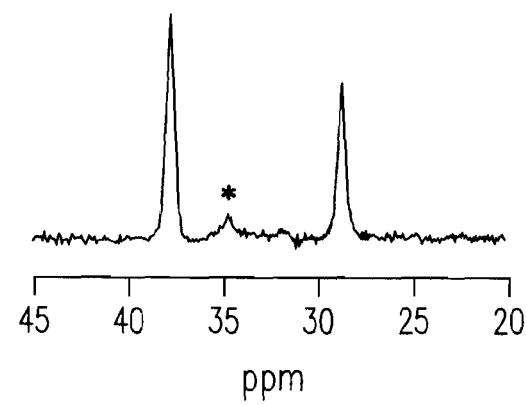
FIG. 10c presents an isotropic projection to the evolution dimension ($F_1$ axis) obtained from the spectrum of FIG. 10a, according to an embodiment of the process of the invention.

FIG. 10a presents an isotropic-anisotropic 2D correlation spectrum obtained from the $^{13}C$ NMR spectrum of adamantine, where $F_2$ and $F_1$ correspond to the chemical shift anisotropic and isotropic shift dimensions, respectively. FIG. 10b presents the chemical shift anisotropic projection obtained by summing all the data onto the acquisition dimension, i.e., the F2 axis. Anisotropic projection equivalent to a spectrum obtained on a stationary sample following a single excitation pulse with high power $^1H$ decoupling can be obtained by summing all the data on to the $F_2$ axis. Half line width, defined as the full width of the peak at the half height position, is 177 Hz, i.e., the anisotropic line width. Here, the chemical shift anisotropy is small. FIG. 10c presents the isotropic projection obtained by summing all the data onto the isotropic shift or evolution dimension (i.e., the F1 axis). The half line width is approximately 30 Hz. The peak labeled "*" is a probe background signal. Results show a line narrowing factor of about six is obtained using SP-DMAT in comparison to the anisotropic line width.

EXAMPLE 3

2D-DMAT and CP-DMAT analyses of 1,2,3-TMB were performed using a Chemagnetics 300 MHz Infinity spectrometer in conjunction with a DMAT probe and DMAT pulse sequence described in Example 1. 2-D data were acquired using following parameters. Rotation speed corresponding to the constant speed rotation segment was 2 Hz, i.e. T=500 ms. The acceleration time (t) was about 110 ms, proceeding from an acceleration of zero initially to 2 Hz was about 110 ms. A first pulse (a) was triggered 4 ms after the 2 Hz speed was reached, leaving a maximum of [500 ms−2T/3−114 ms=52.6 ms] for segments of the sequence, i.e., $(2\tau+t_b/3)$. Given a typical value of ($\tau$=100 µs), value of ($t_b/3$) can be as long as 52.4 ms, resulting in a maximum evolution time of 157.5 ms. Recycle delay time was 5 s. Free-induction decays in the acquisition dimension ($t_2$) contained 128 complex points and were transformed to spectra with a spectral width of 40 kHz. 2-D data were collected using 70 ($t_b$) steps, incremented by 90 µs, corresponding to a maximum evolution time of 6.3 ms and an evolution spectral width of 11.11 kHz. 2-D data sets were acquired with the (+) and the (−) DMAT pulse sequences (see FIG. 1) using a total of 256 scans at each ($t_b$) value, resulting in a total measuring time of 25 hours. The $^1$H ($B_1$) field during both the (CP) and (HPDEC) decoupling periods was about 38 kHz. FIGS. 11a-11c present results obtained from DMAT analysis of 1,2,3-trimethoxybenzene (1,2,3-TMB) samples.

FIG. 11a is a 2-D contour plot of a $^{13}$C CP-DMAT spectrum of 1,2,3-TMB. FIG. 11b is an anisotropic powder pattern obtained by summing all the spectral data onto the $F_2$ plot axis. Anisotropic width, defined as the difference between the principle values of $\delta_{11}$ and $\delta_{33}$, are 145 ppm and 108 ppm, respectively. FIG. 11c presents a high resolution isotropic projection obtained by summing all the spectrum data onto the $F_1$ plot axis. In the figure, the spectrum for 1,2,3-TMB is significantly enhanced owing to the more easily achievable accurate angle setting in a one step rotation used for the DMAT experiment. In the figure, $M_2$ and $M_{1,3}$ peaks corresponding to methoxy moieties are well resolved. Isotropic line widths obtained were about 2 ppm. A line narrowing from 72 to 54 was achieved.

Figure 12A:
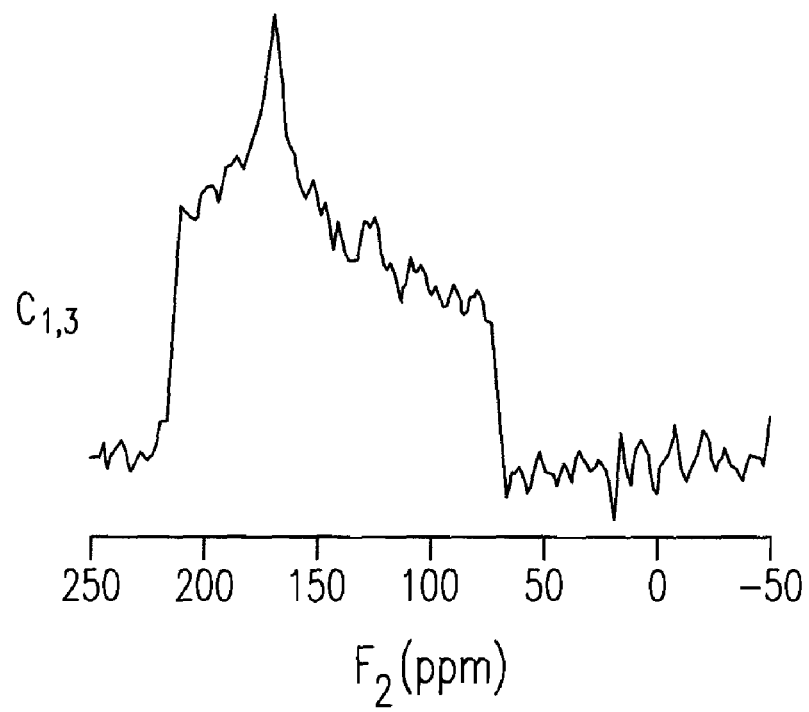
FIG. 12a-12b present sliced chemical shift powder patterns corresponding to carbons $C_{1,3}$ and $C_2$ of the 1,2,3-TMB sample obtained from the 2D-DMAT spectrum of FIG. 11a, according to an embodiment of the process of the invention.
Figure 12B:
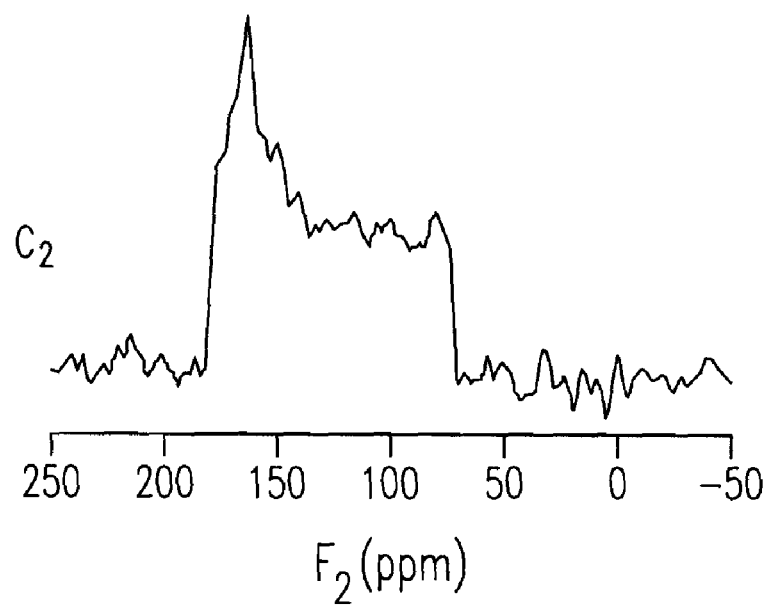

FIGS. 12a-12b show anisotropic powder patterns corresponding to $C_{1,3}$ and $C_2$ carbon peaks from the 2-D DMAT spectra of FIG. 11a. Spectra were obtained by selecting a slice at the center of the isotropic chemical shift position of the peak, in parallel with the $F_2$ plot axis.

EXAMPLE 4

Example 4 provides illustrative computer-executable code to initiate, execute, and control speed profiles in conjunction with DMAT, effecting speed and rotation control of a sample or specimen. Code presented hereafter is exemplary of codes that can be implemented, but is not limited. Instant code is drafted in standard Visual Basic language and specialized speed controller language, but is not limited thereto:

Executable Code

```
Dim RC As Long 'Variable to hold error DMC command responses;
Dim hDmc As Long 'port of controller, set from response to open;
Dim Controller As Integer 'controller number, currently only have one, so will be one;
Dim Response As String*4096 'response string to commands;
Dim ResponseLength As Long 'length of the response string;
Dim ACfor As Long 'AC(Acceleration) for clockwise direction;
Dim Vfor As Long 'peak velocity for clockwise direction;
Dim Xfor As Double 'distance to travel for clockwise direction during acceleration;
Dim DCback As Long 'DC(Deceleration) for clockwise direction;
Dim Vback As Long 'peak velocity for counter-clockwise direction;
Dim Xback As Double 'distance to travel for clockwise direction during deceleration;
'routine used to find acceleration and deceleration numbers; velocity, and distance for ramp up for clockwise direction;
Public Sub find_speed( );
Dim Tfor As Double;
Dim Tback As Double;
Dim Tacc As Double;
Dim Tdec As Double;
Dim Xacc As Double;
Dim Xdec As Double;
Dim factor As Long;
Vfor=Speed 'the final speed for clockwise direction;
Vback=Speed 'the final speed for counter-clockwise direction;
Xfor=((CLng(Rot1.Text)/360)*4000) 'distance needed to travel on ramp up;
Xback=((CLng(Rot3.Text)−CLng(Rot2.Text))/360)*4000 'distance needed to travel on ramp down;
Tfor=(2*Xfor)/Vfor 'time to accelerate to constant speed;
Tback=(2*Xback)/Vback 'time to decelerate to zero speed;
ACfor=Vfor/Tfor 'Acceleration calculation;
If (ACfor<1024) Then 'if acceleration is less than minimum acceleration;
    ACfor=1024 'set acceleration to minimum acceleration;
    Tacc=Vfor/ACfor;
    Xacc=0.5*ACfor*Tacc*Tacc;
    Tfor=(Xfor−Xacc)/Vfor;
    Tfor=Tfor+Tacc 'find new total time to travel distance specified by user;
Else;
    factor=((ACfor+1023)/1024) 'if acceleration is greater than 1024, go to next 1024 factor;
    ACfor=factor*1024;
    Tacc=Vfor/ACfor;
    Xacc=0.5*ACfor*Tacc*Tacc;
    Tfor (Xfor−Xacc)/Vfor;
    Tfor=Tfor+Tacc 'find new total time to travel distance specified by user;
End If;
DCback=Vback/Tback 'deceleration calculation;
If (DCback<1024) Then 'if deceleration is less than minimum deceleration;
    DCback=1024 'set deceleration to minimum deceleration;
    Tdec=Vback/DCback;
    Xdec=0.5*DCback*Tdec*Tdec;
    Tback=(Xback−Xdec)/Vback;
    Tback=Tback+Tdec 'find new total time to travel distance specified by user;
Else;
    factor=((DCback+1023)/1024) 'if acceleration is greater than X;
    DCback=factor*1024;
    Tdec=Vback/DCback;
    Xdec=0.5*DCback*Tdec*Tdec;
    Tback=(Xback−Xdec)/Vback;
```

```
        Tback=Tback+Tdec 'find new total time to travel dis-
            tance specified by user;
    End If;
    Time1.Text=Format((Tfor*1000), "####0.00") 'display
        this time;
    Time2.Text=Format((Tback*1000), "####0.00") 'display
        this time;
End Sub;
'convert Hz constant speed to counts/second;
Public Function Speed( ) As Long;
Dim total As Double;
total=4000*CDbl(CstSpd.Text) 'change hertz into counts
    for speed purposes;
Speed=CLng(total+0.5);
End Function;
'load up main form and initialize the controller;
Private Sub Form_Load( );
Response=Space(256);
ResponseLength=256;
hDmc=-1;
Controller=1;
Start.Enabled=False 'disable the start button;
If Command$ <>"" Then;
    Controller=Val(Command);
End If;
If Controller<1 Or Controller>15 Then;
    Controller=1;
End If;
RC=DMCOpen(Controller, 0, hDmc) 'open up connection
    to controller;
If RC=0 Then;
    RC=DMCVersion(hDmc, Response, ResponseLength);
    VersionBox.Caption=Response;
    RC=DMCCommand(hDmc, ";", Response, Response-
        Length);
    ResponseBox.Text=Response;
Else 'if can't open, give error and unload form;
    hDmc=-1;
    MsgBox "Error: could not connect to controller"+Trim$
        (Str$(Controller))+". RC="+Trim$(Str$(RC));
    Unload Form1;
End If;
End Sub;
'close down form, close down connection, reset programs;
Private Sub Form_Unload(Cancel As Integer);
Timer1.Enabled=False;
send ("RS");
If hDmc <>-1 Then;
    RC=DMCClose(hDmc);
End If;
End Sub;
'run the program, wait for trigger or stop looping;
Private Sub Start_Click( );
If (Start.Caption="Start") Then;
    Start.Caption="Stop" 'change button to a stop button;
    Reset.Enabled=False 'disable reset button;
    Load.Enabled=False 'disable load button;
    Rot1.Enabled=False 'disable rotation input;
    Rot2.Enabled=False 'disable rotation input;
    Rot3.Enabled=False 'disable rotation input;
    CstSpd.Enabled=False 'disable speed input;
    WaitTime.Enabled=False 'disable wait time input;
    send ("XQ#FORWARD") 'start motion program;
ElseIf (Start.Caption="Stop") Then;
    Start.Caption="Start" 'change button to a start button;
    Reset.Enabled=True 'enable the reset ability;
    Load.Enabled=False 'dont allow a new load;
    send ("ST") 'stop motion program;
End If;
End Sub;
Private Sub Reset_Click( );
Send ("RS") 'erase programs from controllers;
Start.Enabled=False 'disable the start button;
Load.Enabled=True 'after reset, allow load of new pro-
    gram;
Rot1.Enabled=True 'enable rotation input change;
Rot2.Enabled=True 'enable rotation input change;
Rot3.Enabled=True 'enable rotation input change;
CstSpd.Enabled=True 'enable speed input change;
WaitTime.Enabled=True 'enable wait time input change;
End Sub;
'load both programs into controller;
Private Sub Load_Click( );
Dim state As String;
Load.Enabled=False 'disable load button;
Call find_speed 'set all the variables for ramp up and ramp
    down;
send ("DP 0") 'reset start position to make current position
    zero;
send ("BL 0");
send ("FL"+CStr(((CLng(Rot3.Text)/360)*4000)));
send ("ED 0") 'go into editor mode;
send ("#FORWARD") 'label start of program;
send ("AI 1") 'wait for TTL pulse into input 1;
send ("PA"+CStr(((CLng(Rot3.Text)/360)*4000))) 'total
    movement wanted;
send ("SP"+CStr(Vfor)) 'speed of rotation;
send ("AC"+CStr(ACfor)) 'acceleration;
send ("DC"+CStr(DCback)) 'deceleration;
send ("BG") 'start motion;
send ("MC") 'after motion completes;
send ("WT"+WaitTime.Text) 'wait for specified time;
send ("PA 0") 'return to start position;
send ("SP"+CStr(Vback)) 'return speed of rotation;
send ("AC"+CStr(DCback)) 'acceleration;
send ("DC"+CStr(ACfor)) 'deceleration;
send ("BG") 'start motion;
send ("MC") 'after motion completes;
send ("AI-1") 'make sure TTL is low;
send ("JP #FORWARD") 'jump back to beginning of pro-
    gram;
send (Chr$(17)) 'code to exit editor "Ctrl-Q";
send ("SH") 'turn motor on;
Start.Enabled=True 'enable the start button;
End Sub;
'send a command over serial port;
Public Function send(com As String);
Dim AdditionalResponse As String;
Response=Space(256);
ResponseLength=256;
RC=DMCCommand(hDmc, corm, Response, Response-
    Length);
RTrim (Response);
If Len(ResponseBox.Text)>32000 Then;
    ResponseBox.Text=com+Chr$(13)+Chr$(10)+Re-
        sponse;
Else;
    ResponseBox.Text=ResponseBox.Text+com+Chr$
        (13)+Chr$(10)+Response;
End If;
If RC=DMCERROR_BUFFERFULL Then;
    RC=DMCGetAdditionalResponseLen(hDmc, Respon-
        seLength);
    If RC=0 Then;
```

```
        AdditionalResponse=Space$(ResponseLength+1);
        RC=DMCGetAdditionalResponse(hDmc, Addition-
           alResponse, ResponseLength);
        RTrim (AdditionalResponse);
        If Len(ResponseBox.Text)>32000 Then;
           ResponseBox.Text=Additional Response;
        Else;
           ResponseBox.Text=ResponseBox.Text+Addition-
              alResponse;
        End If;
     End If;
  End If;
  ResponseBox.SelStart=Len(ResponseBox.Text);
  End Function;
  Private Sub Timer1_Timer( );
  Dim Pos As Integer;
  Response=Space(256);
  ResponseLength=256;
  RC=DMCGetUnsolicitedResponse(hDmc,       Response,
     ResponseLength);
  RTrim (Response) 'Trim spaces;
  Pos=InStr(Response, Chr$(0)) 'Discard responses which
     consist of only NULL characters;
  If Len(Response)>0 And Pos>1 Then;
     If Len(ResponseBox.Text)>32000 Then;
        ResponseBox.Text=Response;
     Else;
        ResponseBox.Text=ResponseBox.Text+Chr$(13)+
           Chr$(10)+Response;
     End If;
     ResponseBox.SelStart=Len(ResponseBox.Text);
  End If;
  End Sub;
  END.
```

CONCLUSIONS

Results with discrete magic angle turning (DMAT) demonstrate that use of a constant speed of rotation during only the evolution period of clockwise and/or counterclockwise rotation directions yield high-resolution, chemical shift anisotropic-isotropic 2D correlation spectra at least equivalent to, and frequently better than, those obtained in a single, continuous rotation direction at a stable speed described previously, e.g., by Gan Z. [J. Am. Chem. Soc. 1992; 114: 8307-8309], Hu et al. [Solid State NMR 3, 181-197 (1994)], Hu et al. [J. Magn. Reson. A113, 210-222 (1995)], Hu et al. [J. Magn. Reson. 163, 149-162 (2003)], and Wind et al. [Magn. Reson. Med. 55, 41-49 (2006)]. DMAT provides new advantages, including, but not limited to, ability to introduce feed lines and/or tubes into the sample rotor, permitting in situ control over temperature, pressure, flow conditions, feed compositions, and the like, in real time, providing a new methodology applicable to a variety of in situ investigations. While the preferred embodiment of the present invention has been shown and described, it will be apparent to those skilled in the art that many changes and modifications may be made without departing from the invention. All configurations and processes as will be contemplated by those of skill in the art in view of the disclosure are within the scope of the invention. No limitations are intended.

We claim:

1. A discrete magic angle turning (DMAT) system for in situ Magnetic Resonance Spectroscopy and Imaging, the system comprising:

a discrete magic angle turning (DMAT) device having a rotor assembly that provides rotation of a sample or specimen in a clockwise and an anti-clockwise rotation direction through a rotation angle greater than or equal to about 240 degrees and less than or equal to about 360 degrees, the rotation of the sample or the specimen is provided about an axis inclined at an angle of 54°44' relative to a static magnetic field ($B_0$) in a radio frequency (RF) magnetic field ($B_1$) that is pulsed in conjunction with an RF pulse sequence or segment; and a speed controlling device operably coupled that synchronizes rotation of the sample or specimen at constant speed through the rotation angle during the evolution period of the RF pulse sequence or segment.

2. The system of claim 1, wherein the DMAT device includes a rotor that inserts into an RF coil for rotation of the sample or specimen therein.

3. The system of claim 2, wherein the sample or specimen rotor is configured with transfer and/or feed lines providing for introduction of chemicals, reagents, fluids, compositions, constituents, mixtures, gases, or combinations of same thereto and/or retrieving same therefrom.

4. The system of claim 3, wherein the gases introduced to, or retrieved from, the sample rotor provide for pressurization control of the rotor and/or samples or specimens introduced thereto.

5. The system of claim 3, wherein constituents introduced to, or retrieved from, the sample or specimen rotor including liquids, reagents, catalysts, and/or combinations thereof provide compositional control of samples or specimens introduced thereto for analysis of same.

6. The system of claim 1, further comprising a computer operably coupled to the DMAT device for measurement, collection, and analysis of spectroscopic and imaging data acquired therewith.

7. The system of claim 1, wherein the speed controlling device is programmable and/or computer-controlled operable for receiving and executing speed profiles programmed therein.

8. The system of claim 1, further comprising a computer operably coupled to the speed controlling device for displaying speed parameters, speed profiles, pulse sequence or segment data, combinations thereof, and data collected therefrom.

9. The system of claim 1, wherein the speed controlling device includes a speed profile that provides an acceleration period that provides a smooth acceleration of the rotor assembly and the sample or specimen therein to a constant speed of rotation, and a deceleration period that provides a smooth deceleration of the rotor assembly and the sample or specimen therein following rotation to a static state prior to rotation in a subsequent opposite rotation direction.

10. The system of claim 1, wherein the DMAT device includes an axis adjustment device operably attached to the rotor assembly for selecting and adjusting directional axis and/or rotation angle of the rotor assembly.

11. The system of claim 1, further includes a detector that provides transistor-to-transistor support logic adapted to trigger and execute the RF pulse sequence or segment in synchronization with precision markers located on, or mounted to, a sample rotor that inserts into an RF coil of the rotor assembly.

12. The system of claim 11, wherein the detector is an optical detector.

13. The system of claim 1, wherein the driving assembly includes a digital encoder adapted for control of rotation angle and rotation direction of the sample rotor in the rotor assembly.

14. The system of claim 1, wherein the sample or specimen is a member selected from the group consisting of fluid objects, biological objects, cells, cell clusters, cell aggregates, tissues, organs, live animals, mounted specimens, and combinations thereof.

15. The system of claim 1, wherein the evolution period is synchronized to begin at least by the start of the RF pulse sequence or segment and to finish at least by the end of the RF pulse sequence or segment.

16. The system of claim 1, wherein the RF pulse sequence or segment includes a PHORMAT pulse.

17. The system of claim 1, wherein the pulse sequence or segment is an HPDEC pulse sequence or segment for decoupling proton signals for $^{13}$C analysis of a solid.

18. The system of claim 1, wherein the sample or specimen is rotated at a rotational frequency selected in the range from about 2 Hz to about 3 Hz during the evolution period of the RF pulse sequence or segment.

19. The system of claim 1, wherein the sample or specimen is rotated at a rotational frequency of up to about 40 Hz during the evolution period of the RF pulse sequence or segment.

20. The system of claim 1, wherein the sample or specimen is rotated at a rotational frequency selected in the range from 0.01 Hz to about 40 Hz during the evolution period of the RF pulse sequence or segment.

21. The system of claim 1, wherein the sample or specimen is rotated at a rotational frequency selected in the range from about 1 Hz to about 100 Hz during the evolution period of the RF pulse sequence or segment.

22. The system of claim 1, wherein the driving assembly operably couples to the DMAT device via one or more pulleys of substantially equal dimension on each such that speed and rotation of the rotor assembly for rotation of the sample or specimen is substantially identical to the speed profile of the driving assembly controlled via programming by the speed controlling device.

23. A discrete magic angle turning (DMAT) device for in situ Magnetic Resonance Spectroscopy and Imaging, comprising:
   a rotor assembly that provides rotation of a sample or a specimen in a clockwise and an anti-clockwise rotation direction through a rotation angle greater than or equal to about 240 degrees and less than or equal to about 360 degrees in conjunction with an RF pulse sequence or segment; and
   a speed controlling device operably coupled to the rotor assembly that synchronizes rotation of the sample or specimen during an evolution period of the RF pulse sequence or segment at a constant speed through the rotation angle.

24. The device of claim 23, further includes a rotor that inserts into an RF coil for rotation of the sample or specimen therein.

25. The device of claim 24, wherein the sample rotor is adapted for attaching transfer and/or feed lines providing for introduction of chemicals, reagents, fluids, compositions, constituents, mixtures, gases, and combinations of same thereto and/or retrieving same therefrom.

26. The device of claim 23, further comprising a driving assembly operably coupled to the apparatus providing rotation of the rotor assembly.

27. The device of claim 26, wherein the driving assembly includes a digital encoder adapted for control of rotation angle and rotation direction of the sample rotor introduced to the rotor assembly.

28. The device of claim 23, further comprising a directional axis device operably attached to the rotor assembly for selecting and adjusting the directional axis and/or rotation angle the rotor assembly.

29. The device of claim 23, further comprising a computer operably coupled for measurement, collection, and analysis of spectroscopic and imaging data acquired therewith.

30. The device of claim 23, further includes a computer-controlled detector adapted to trigger and execute the RF pulse sequence or segment that provides transistor-to-transistor support logic in synchronization with precision markers located on, or mounted to, a sample rotor that inserts into an RF coil of the rotor assembly.

31. The device of claim 23, wherein the specimen is a member selected from the group consisting of fluid objects, biological objects, cells, cell clusters, cell aggregates, tissues, organs, live animals, mounted specimens, and combinations thereof.

32. The device of claim 23, wherein the period at constant speed is synchronized to begin at least by the start of the RF pulse segment and to finish at least by the end of the RF pulse segment.

33. The device of claim 23, wherein the RF pulse sequence or segment includes a PHORMAT pulse sequence or segment, or an SP-PHORMAT pulse sequence or segment.

34. The device of claim 23, wherein the RF pulse sequence or segment provides pulses selected from the group consisting of: PHORMAT, SP-PHORMAT, HPDEC, CHESS, DANTE, WET, and combinations thereof.

35. The device of claim 23, wherein the RF pulse sequence is an HPDEC pulse sequence for decoupling proton signals for $^{13}$C analysis of a solid.

36. The device of claim 23, wherein the sample or specimen is rotated at a rotational frequency selected in the range from about 2 Hz to about 3 Hz during the evolution period of the RF pulse sequence or segment.

37. The device of claim 23, wherein the sample or specimen is rotated at a rotational frequency of up to about 40 Hz during the evolution period of the RF pulse sequence or segment.

38. The device of claim 23, wherein the sample or specimen is rotated at a rotational frequency selected in the range from 0.01 Hz to about 40 Hz during the evolution period of the RF pulse sequence or segment.

39. The device of claim 23, wherein the sample or specimen is rotated at a rotational frequency selected in the range from about 1 Hz to about 100 Hz during the evolution period of the RF pulse sequence or segment.

40. A method for performing discrete magic angle turning (DMAT) for in situ Magnetic Resonance Spectroscopy and Imaging, comprising the steps:
   rotating a sample or specimen in a clockwise and an anti-clockwise rotation direction through a rotation angle greater than or equal to about 240 degrees and less than or equal to about 360 degrees about an axis while inclined at an angle of 54°44' relative to a static magnetic field ($B_0$) in a radio frequency (RF) magnetic field ($B_1$);
   pulsing the RF magnetic field with an RF pulse sequence or segment during rotation of the sample or the specimen; and
   synchronizing rotation of the sample or specimen at a constant speed during the evolution period of the RF pulse sequence or segment through the rotation angle.

41. The method of claim 40, further including the step of acquiring spectroscopic data during the evolution period, wherein correlation between a high resolution peak and a low resolution peak in a two dimensional spectral plane provides information for analyzing the sample or specimen.

42. The method of claim 40, wherein the RF pulse sequence or segment includes pulses selected from the group consisting of: PHORMAT, SP-PHORMAT, HPDEC, CHESS, DANTE, WET, and combinations thereof.

43. The method of claim 40, wherein the speed profile includes an acceleration period providing smooth acceleration of the sample or specimen to a constant speed of rotation, and/or a deceleration period providing a smooth deceleration of the sample or specimen following rotation to a static state prior to rotation in a subsequent opposite rotation direction.

44. The method of claim 40, wherein the step of synchronizing the rotation of the sample or specimen includes use of a speed profile that provides an acceleration period employed prior to initiation of the constant speed period for ramping the speed of rotation in the counterclockwise rotation direction to match the speed selected for the period at constant speed and a deceleration period employed subsequent to the period of constant speed for decreasing the speed of rotation of the sample or specimen to a substantially stopped position prior to a subsequent rotation in the counterclockwise rotation direction.

45. The method of claim 40, wherein the pulse sequence comprises a HPDEC pulse segment for decoupling proton signals for $^{13}$C analysis of a solid.

46. The method of claim 40, wherein the sample or specimen is rotated at a rotational frequency selected in the range from about 2 Hz to about 3 Hz, or a rotational frequency selected in the range from about 1 Hz to about 100 Hz during the evolution period of the RF pulse sequence or segment.

47. The method of claim 40, wherein the sample or specimen is rotated at a rotational frequency less than about 100 Hz in conjunction with a 2D-PASS pulse segment.

48. The method of claim 40, wherein the pulse segment is utilized in conjunction with a $^1$H-proton NMR analysis.

49. A method for performing discrete magic angle turning (DMAT) for in situ Magnetic Resonance Spectroscopy and Imaging, characterized by the steps of:

rotating a sample or specimen about an axis inclined at a magic angle in a clockwise and an anti-clockwise rotation direction at a constant speed through a rotation angle greater than or equal to about 240 degrees and less than or equal to about 360 degrees in conjunction with a RF pulse sequence or segment; and synchronizing rotation of the sample or specimen at a constant speed during an evolution period of the RF pulse sequence or segment through the rotation angle.

* * * * *